(12) United States Patent
Gaudriault et al.

(10) Patent No.: US 11,865,205 B2
(45) Date of Patent: Jan. 9, 2024

(54) METHOD FOR MORSELIZING AND/OR TARGETING PHARMACEUTICALLY ACTIVE PRINCIPLES TO SYNOVIAL TISSUE

(71) Applicant: MEDINCELL, Jacou (FR)

(72) Inventors: Georges Gaudriault, Montpellier (FR); Sylvestre Grizot, Le Crès (FR); Mark Hurtig, Ontario (CA); Matthew Shive, Denver, CO (US)

(73) Assignee: MEDINCELL S.A., Jacou (FR)

( * ) Notice: Subject to any disclaimer, the term of this patent is extended or adjusted under 35 U.S.C. 154(b) by 0 days.

(21) Appl. No.: 17/156,781

(22) Filed: Jan. 25, 2021

(65) Prior Publication Data
US 2021/0322302 A1 Oct. 21, 2021

Related U.S. Application Data

(63) Continuation of application No. 15/776,355, filed as application No. PCT/IB2016/001815 on Nov. 16, 2016, now abandoned.

(60) Provisional application No. 62/255,778, filed on Nov. 16, 2015.

(51) Int. Cl.
| | |
|---|---|
| *A61K 9/00* | (2006.01) |
| *A61P 19/02* | (2006.01) |
| *A61K 31/415* | (2006.01) |
| *A61K 45/06* | (2006.01) |
| *A61K 47/34* | (2017.01) |

(52) U.S. Cl.
CPC .......... *A61K 9/0024* (2013.01); *A61K 31/415* (2013.01); *A61K 45/06* (2013.01); *A61K 47/34* (2013.01); *A61P 19/02* (2018.01)

(58) Field of Classification Search
None
See application file for complete search history.

(56) References Cited

U.S. PATENT DOCUMENTS

| | | | |
|---|---|---|---|
| 3,043,832 A | 7/1962 | Ruggieri et al. | |
| 3,377,364 A | 4/1968 | Spero | |
| 4,526,938 A | 7/1985 | Churchill et al. | |
| 4,745,160 A | 5/1988 | Churchill et al. | |
| 4,938,763 A | 7/1990 | Dunn et al. | |
| 5,077,049 A | 12/1991 | Dunn et al. | |
| 5,221,534 A | 6/1993 | Deslauriers et al. | |
| 5,278,201 A | 1/1994 | Dunn et al. | |
| 5,278,202 A | 1/1994 | Dunn et al. | |
| 5,340,849 A | 8/1994 | Dunn et al. | |
| 5,518,730 A | 5/1996 | Fuisz | |
| 5,548,035 A | 8/1996 | Kim et al. | |
| 5,632,727 A | 5/1997 | Tipton et al. | |
| 5,733,950 A | 3/1998 | Dunn et al. | |
| 5,739,176 A | 4/1998 | Dunn et al. | |
| 5,744,153 A | 4/1998 | Yewey et al. | |
| 5,780,044 A | 7/1998 | Yewey et al. | |
| 5,990,194 A | 11/1999 | Dunn et al. | |
| 6,143,314 A | 11/2000 | Chandrashekar et al. | |
| 6,194,006 B1 | 2/2001 | Lyons et al. | |
| 6,206,920 B1 | 3/2001 | Eliaz et al. | |
| 6,261,583 B1 | 7/2001 | Dunn et al. | |
| 6,294,204 B1 | 9/2001 | Rossling et al. | |
| 6,350,812 B1 | 2/2002 | Vert et al. | |
| 6,379,703 B1 | 4/2002 | Lyons et al. | |
| RE37,950 E | 12/2002 | Dunn et al. | |
| 6,565,874 B1 | 5/2003 | Dunn et al. | |
| 6,592,899 B2 | 7/2003 | Fowers et al. | |
| 6,596,318 B2 | 7/2003 | Lyons et al. | |
| 6,630,155 B1 | 10/2003 | Chandrashekar et al. | |
| 6,667,061 B2 | 12/2003 | Ramstack et al. | |
| 6,773,714 B2 | 8/2004 | Dunn et al. | |
| 6,916,788 B2 | 7/2005 | Seo et al. | |
| 7,019,106 B2 | 3/2006 | Yamamoto et al. | |
| 7,153,520 B2 | 12/2006 | Seo et al. | |
| 7,160,551 B2 | 1/2007 | McHugh et al. | |
| 7,301,001 B2 | 11/2007 | Hossainy et al. | |
| 7,371,406 B2 | 5/2008 | Ramstack et al. | |
| 7,649,023 B2 | 1/2010 | Shih et al. | |
| 8,221,778 B2 | 7/2012 | Siegel et al. | |
| 8,642,666 B2 | 2/2014 | Shih et al. | |

(Continued)

FOREIGN PATENT DOCUMENTS

| | | |
|---|---|---|
| CA | 2530003 A1 | 12/2004 |
| CA | 2822854 A1 | 7/2012 |

(Continued)

OTHER PUBLICATIONS

Cerrai et al., "Block copolymers of L-lactide and poly(ethylene glycol) for biomedical applications", Journal of Materials Science: Materials in Medicine, vol. 5 (1994) pp. 308-313.
International Search Report issued in International Application No. PCT/IB2011/003323 dated Aug. 9, 2012.
Li, "Bioresorbable Hydrogels Prepared Through Stereocomplexation between Poly (L-lactide) and Poly (D-lactide) Blocks Attached to Poly(ethylene glycol)", Macromolecular Bioscience, vol. 3, No. 11 (2003) pp. 657-661.
Baimark et al., "Biodegradable nanoparticles of methoxy poly(ethylene glycol)-b-poly(D,L-lactide)/methoxy poly(ethylene glycol)-b-poly(E-caprolactone) blends for drug delivery," Nanoscale Research Letters, vol. 7, No. 271, May 30, 2012, pp. 1-8.
Bédouet et al., "Intra-articular Fate of Degradable Poly(ethyleneglycol)-hydrogel Microspheres as Carriers for Sustained Drug Delivery", International Journal of Pharmaceutics, vol. 456, No. 2 (2013) pp. 536-544.

(Continued)

*Primary Examiner* — Robert A Wax
*Assistant Examiner* — William Craigo
(74) *Attorney, Agent, or Firm* — Birch, Stewart, Kolasch & Birch, LLP

(57) ABSTRACT

A method of targeting to the synovial tissue biodegradable drug delivery compositions or morselizing biodegradable drug delivery compositions are described. The biodegradable drug composition comprises a triblock copolymer containing a polyester and a polyethylene glycol and a diblock copolymer containing a polyester and an end-capped polyethylene glycol, as well as at least one pharmaceutically active principle is disclosed.

19 Claims, 7 Drawing Sheets
(3 of 7 Drawing Sheet(s) Filed in Color)

(56) References Cited

U.S. PATENT DOCUMENTS

| | | | |
|---|---|---|---|
| 8,741,327 B2 | 6/2014 | Siegel et al. | |
| 8,802,127 B2 | 8/2014 | Siegel et al. | |
| 8,852,638 B2 | 10/2014 | Luk et al. | |
| 9,023,897 B2 | 5/2015 | Gaudriault | |
| 9,044,450 B2 | 6/2015 | Luk et al. | |
| 9,265,836 B2 | 2/2016 | Shih et al. | |
| 9,393,310 B2 | 7/2016 | Zale et al. | |
| 9,439,905 B2 | 9/2016 | Siegel et al. | |
| 9,579,386 B2 | 2/2017 | Zale et al. | |
| 9,717,799 B2 | 8/2017 | Siegel et al. | |
| 9,895,447 B2 | 2/2018 | Siegel et al. | |
| 9,925,268 B2 | 3/2018 | Siegel et al. | |
| 10,111,960 B2 | 10/2018 | Siegel et al. | |
| 2002/0028249 A1 | 3/2002 | Rickey et al. | |
| 2003/0068377 A1 | 4/2003 | Fowers et al. | |
| 2003/0139353 A1 | 7/2003 | Jackson et al. | |
| 2003/0228366 A1 | 12/2003 | Shih et al. | |
| 2004/0001872 A1 | 1/2004 | Shih et al. | |
| 2004/0037885 A1 | 2/2004 | Seo et al. | |
| 2004/0185104 A1 | 9/2004 | Piao et al. | |
| 2005/0112170 A1 | 5/2005 | Hossainy et al. | |
| 2006/0034889 A1 | 2/2006 | Jo et al. | |
| 2007/0104759 A1 | 5/2007 | Dunn et al. | |
| 2008/0247987 A1* | 10/2008 | Liggins | A61K 9/0014 424/78.17 |
| 2008/0305140 A1 | 12/2008 | Siegel et al. | |
| 2009/0004243 A1 | 1/2009 | Pacetti et al. | |
| 2009/0264472 A1 | 10/2009 | Wohabrebbi et al. | |
| 2012/0172454 A1* | 7/2012 | Gaudriault | A61K 38/26 514/772.1 |
| 2016/0310801 A1 | 10/2016 | Thanoo et al. | |
| 2017/0196855 A1 | 7/2017 | Ahmed et al. | |
| 2019/0105396 A1 | 4/2019 | Siegel et al. | |
| 2019/0167839 A1 | 6/2019 | Shalaby et al. | |

FOREIGN PATENT DOCUMENTS

| | | |
|---|---|---|
| CA | 2877083 A1 | 1/2014 |
| CA | 2938019 A1 | 7/2015 |
| CN | 101810580 A | 8/2010 |
| EP | 0343850 A2 | 11/1989 |
| EP | 0436667 B1 | 4/1997 |
| EP | 1125577 A2 | 8/2001 |
| EP | 0773034 B1 | 12/2002 |
| EP | 1126822 B1 | 2/2004 |
| EP | 1322286 B1 | 5/2005 |
| EP | 1586309 A1 | 10/2005 |
| EP | 1100460 B1 | 4/2008 |
| EP | 1339389 B1 | 8/2008 |
| EP | 2359880 A2 | 8/2011 |
| FR | 2741628 A1 | 5/1997 |
| GB | 866381 A | 4/1961 |
| JP | 2-242996 A | 9/1990 |
| JP | 7-507548 A | 8/1995 |
| JP | 9-505286 A | 5/1997 |
| JP | 9-208494 A | 8/1997 |
| JP | 2000-503663 A | 3/2000 |
| JP | 2000-514457 A | 10/2000 |
| JP | 2003-525243 A | 8/2003 |
| JP | 2005-524730 A | 8/2005 |
| JP | 2005-535638 A | 11/2005 |
| JP | 2007-512094 A | 5/2007 |
| JP | 2007-513226 A | 5/2007 |
| JP | 2008-510004 A | 4/2008 |
| JP | 2008-542293 A | 11/2008 |
| JP | 2009-515669 A | 4/2009 |
| JP | 2010-513954 A | 4/2010 |
| JP | 2010-215562 A | 9/2010 |
| JP | 2011-518187 A | 6/2011 |
| JP | 2012-509318 A | 4/2012 |
| MX | 2013007682 A | 10/2013 |
| WO | WO 88/02625 A1 | 4/1988 |
| WO | WO 93/00070 A1 | 1/1993 |
| WO | WO 93/24154 A1 | 12/1993 |
| WO | WO 95/03357 A1 | 2/1995 |
| WO | WO 95/13814 A1 | 5/1995 |
| WO | WO 96/21427 A1 | 7/1996 |
| WO | WO 97/10849 A1 | 3/1997 |
| WO | WO 98/02171 A1 | 1/1998 |
| WO | WO 99/21908 A1 | 5/1999 |
| WO | WO 01/45742 A1 | 6/2001 |
| WO | WO 01/82970 A1 | 11/2001 |
| WO | WO 02/45889 A1 | 6/2002 |
| WO | WO 03/017990 A2 | 3/2003 |
| WO | WO 03/041885 A1 | 5/2003 |
| WO | WO 03/093344 A1 | 11/2003 |
| WO | WO 2005/051449 A1 | 6/2005 |
| WO | WO 2005/054319 A1 | 6/2005 |
| WO | WO 2005/070332 A1 | 8/2005 |
| WO | WO 2006/127953 A2 | 11/2006 |
| WO | WO 2007/011955 A2 | 1/2007 |
| WO | WO 2007/019439 A2 | 2/2007 |
| WO | WO 2007/081896 A1 | 5/2007 |
| WO | WO 2008/076729 A1 | 6/2008 |
| WO | WO 2008/153611 A2 | 12/2008 |
| WO | WO 2009/060473 A2 | 5/2009 |
| WO | WO 2009/129509 A2 | 10/2009 |
| WO | WO 2009/132050 A2 | 10/2009 |
| WO | WO 2011/154724 A2 | 12/2011 |
| WO | WO 2012/090070 A2 | 7/2012 |
| WO | WO 2012/131106 A1 | 10/2012 |
| WO | WO 2014/001904 A1 | 1/2014 |
| WO | WO 2018/015915 A1 | 1/2018 |
| WO | WO 2018/227293 A1 | 12/2018 |

OTHER PUBLICATIONS

Chen et al., "In vitro release of levonorgestrel from phase sensitive and thermosensitive smart polymer delivery systems," Pharmaceutilal development and technology, vol. 10, No. 2, 2005, pp. 319-325 (2 pages, Abstract only).

Fang et al., "Acute Toxicity evaluation of in situ gel-forming controlled drug delivery system based on biodegradable poly(E-caprolactone)-poly(ethylene glycol)-poly(E-caprolactone) copolymer," Biomed. Mater., vol. 4, No. 2, Feb. 11, 2009, 2 pages (abstract only).

Fujiwara et al., "Novel Thermo-Responsive Formation of a Hydrogel by Stereo-Complexation between PLLA-PEG-PLLA and PDLA-PEG-PDLA Block Copolymers," Macromol. Biosci., vol. 1, No. 5, 2001, pp. 204-208.

Higaki, "Recent development of nanomedicine for the treatment of inflammatory diseases," Inflammation and Regeneration, vol. 29, No. 2, Mar. 2009, pp. 112-117.

International Preliminary Report on Patentability issued in corresponding PCT Application No. PCT/IB2016/001815 dated May 31, 2018.

International Search Report for International Application No. PCT/IB2013/001547, dated Dec. 3, 2013.

International Search Report issued in corresponding PCT Application No. PCT/IB2016/001815 dated Feb. 27, 2017.

Mao et al., "in Situ Formation and Gelation Mechanism of Thermoresponsive Stereocomplexed Hydrogels Upon Mixing Diblock and Triblock Poly(lactic Acid)/Poly(ethylene Glycol) Copolymers," J Phys Chem B, vol. 119, No. 21, May 14, 2015, pp. 6471-6480 (Abstract only).

McKenzie et al., "Proof-of-Concept of Polymeric Sol-Gels in Multi-Drug Delivery and Intraoperative Image-Guided Surgery for Peritoneal Ovarian Cancer," Pharm Res, Jun. 9, 2016, 9 pages.

Petit et al., "Sustained Intra-Articular Replease of Celecoxib from in situ Forming Gels Made of Acetyl-Capped PCLA-PEG-PCLA Triblock Copolymers in Horses", Biomaterials, vol. 53 (2015) pp. 426-436.

Singaporean Search Report for Singaporean Application No. 11201408658P, dated Dec. 23, 2015.

Yu et al., "Biodegradability and Biocompatibility of Thermoreversible Hydrogels Formed from Mixing a Sol and a Precipitate of a Block Copolymers in Water," Biomacromolecules, vol. 11, No. 8, 2010 (published online Jul. 15, 2010), pp. 2169-2178.

(56) References Cited

OTHER PUBLICATIONS

Yu et al., "Mixing a Sol and a Precipitate of a Block Copolymers with Different Block Ratios Leads to an Injectable Hydrogel," Biomacromolecules, vol. 10, No. 6, 2009 (published online Apr. 22, 2009), pp. 1547-1553.

* cited by examiner

Distribution – Macroscopic Appearance from day 1 to day 40

FIGURE 5A

| Formulation ID | Animal # | In vivo macroscopic observation | Morselization? | Detailed in vivo observation on the depot |
|---|---|---|---|---|
| F390 | #1 | 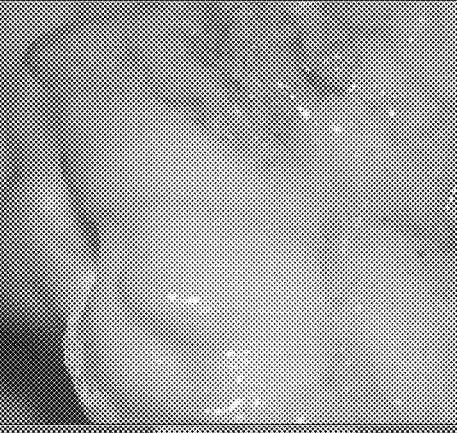 | YES | Widespread distribution to all compartments<br>No free aggregates in synovial space/fluid were present<br>Larger aggregates in the anterior fat pad<br>Deeper penetration into the synovial soft tissue in other locations |
| F391 | #2 | 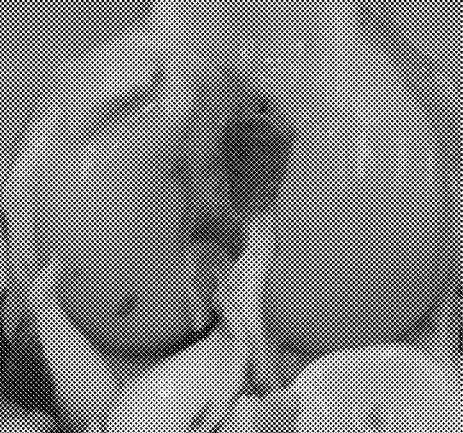 | NO | Distribution to Anterior, posterior and suprapatellar compartments<br>Single large free aggregates with some small particles<br>Limited uptake by the synovial membrane<br>Part of these injection was found in soft tissue immediately adjacent to the synovial space |
| F392 | #3 | 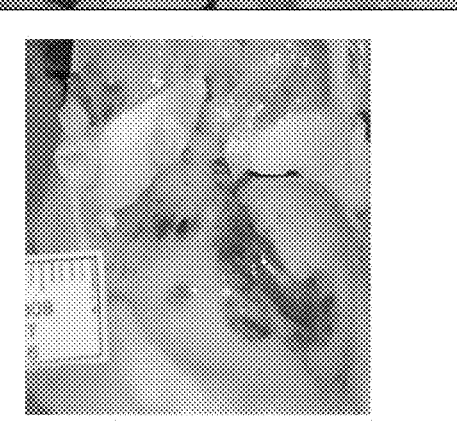 | YES | Widespread distribution to all compartments<br>Some aggregates were encapsulated and intake but not degraded- some resistance to degradation?<br>Small particles and larger aggregates attached or within the synovial membrane.<br>In some locations uptake into the synovial membrane was evident but slower than some other formulations. |

FIGURE 5B

| F393 | #4 | | YES | Extensive distribution with no free aggregates in the synovial space<br>Widespread uptake of polymer into synovial membrane with early degradation<br>Some larger aggregates within 1-2 mm of the synovial membrane surface<br>Early and effective morselization an uptake into soft tissue |
| --- | --- | --- | --- | --- |
| F394 | #5 | | NO | No morselization, limited distribution<br>Appeared as large solitary aggregates resembling polyethyelene<br>Capable of deformation between joint surfaces & residency there (undesirable)<br>No soft tissue uptake |
| F395 | #6 | | YES | Widespread distribution to all compartments<br>Larger aggregates in the anterior fat pad<br>Deeper penetration into the synovial soft tissue |

FIGURE 5C

| F396 | #7 | | YES | Completely morselized and no residual aggregates free in the joint spaces. The formulation was distributed to all joint compartments including the lateral, medial and posterior gutters, the patellofemoral, suprapatellar and femorotibial joint spaces |
| F14 | #8 | | YES | Widespread distribution to all compartments<br>No free aggregates in synovial space/fluid were present<br>Larger aggregates in the anterior fat pad<br>Deeper penetration into the synovial soft tissue in other locations |

US 11,865,205 B2

METHOD FOR MORSELIZING AND/OR TARGETING PHARMACEUTICALLY ACTIVE PRINCIPLES TO SYNOVIAL TISSUE

CROSS REFERENCE TO RELATED APPLICATIONS

This application is a Continuation of U.S. patent application Ser. No. 15/776,355, filed May 15, 2018, which is the National Phase of PCT International Application No. PCT/162016/001815, filed on Nov. 16, 2016, which claims priority under 35 U.S.C. 119(e) to U.S. Provisional Application No. 62/255,778, filed on Nov. 16, 2015, all of which are hereby expressly incorporated by reference into the present application.

FIELD OF THE INVENTION

The present invention relates to a method for morselizing and/or targeting at least one pharmaceutically active principle to synovial tissue and/or other joint tissue such as articular cartilage, ligaments, tendons, meniscus, and the like by administering a biodegradable drug delivery composition comprising a triblock copolymer containing a polyester and a polyethylene glycol and a diblock copolymer containing a polyester and one end-capped polyethylene glycol.

BACKGROUND OF THE PRESENT INVENTION

Arthritis is a general term for conditions that affect the joints and surrounding tissues. Joints are places in the body where bones come together, such as the knees, wrists, fingers, toes, and hips. The two most common types of arthritis are osteoarthritis and rheumatoid arthritis.

Osteoarthritis is the most common type of joint disease, affecting more than 20 million individuals in the United States alone. It is the leading cause of chronic disability in those older than 70 years, costing the U.S. greater than $185 billion annually. It is a painful, degenerative joint disease that often involves the hips, knees, neck, lower back, or small joints of the hands. Osteoarthritis usually develops in joints that are injured by repeated overuse from performing a particular task or playing a favorite sport or from carrying around excess body weight.

Osteoarthritis can be thought of as a degenerative disorder arising from the biochemical breakdown of articular (hyaline) cartilage in the synovial joints. However, the current view holds that osteoarthritis involves not only the articular cartilage but the entire joint organ, including the subchondral bone and synovium.

Rheumatoid arthritis is an autoimmune inflammatory disease that usually involves various joints in the fingers, thumbs, wrists, elbows, shoulders, knees, feet, and ankles. An autoimmune disease is one in which the body releases antibodies and enzymes that attack its own healthy tissues. In rheumatoid arthritis, these enzymes destroy the linings of joints. This causes pain, swelling, stiffness, malformation, and reduced movement and function.

For example, in rheumatoid arthritis, unregulated chemokine accumulation in bone joints attracts and activates infiltrating macrophages and T cells. The activities of these cells induce synovial cell proliferation that leads, at least in part, to inflammation and eventual bone and cartilage loss (see, DeVries, M. E., et al., Semin Immunol 11(2): 95-104 (1999)).

Gout is a disease resulting from the deposition of monosodium urate crystals in synovial fluid and other tissues or the formation of uric acid stones in the kidney. Gout typically occurs during middle age and is uncommon before the age of 30 years. Women rarely have gouty arthritis attacks before menopause.

Moreover, more than 100 diseases can be classified as rheumatic diseases such as ankylosing sondylitis, fibromyalagia, infectious arthritis, juvenile idiopathic arthritis, lupus erythematosus, polymyalgia rheumatica, psoriatic arthritis, reactive arthritis and sclerodoma. These rheumatic diseases involve the joints by causing wear and tear arthritis, infection autoimmune disorders or crystal diseases such as gout.

Generally, arthritis and other rheumatic diseases characterized by chronic musculoskeletal pain and diverse forms of acute pain are treated with nonsteroidal anti-inflammatory drugs (NSAIDs). NSAIDs act by blocking production of prostaglandins by inhibiting the activity of the enzyme PGG/H synthase, also known as cyclooxygenase (COX). COX occurs in two isoforms; i.e., COX-1 and COX-2 which differ in their regulation and tissue distribution. COX-1 is expressed under basal conditions and is involved in the biosynthesis of PG serving homeostatic functions. COX-2 expression is increased during some pathological conditions and inflammation (Crofford et al *Arthritis Rheum* (2000), 43:4-13).

U.S. Pat. No. 8,557,865 B2 discloses a method for treating osteoarthritis with ion channel regulators of verapamil, diltiazem, nifedipine, procainimide, tetrodotoxin and mixtures thereof. This method comprises injecting these ion-channel regulators in an intra-articular space of a joint of a patient.

Thakkar et al, *Drugs R D* (2007):8 (5) 275-285 disclose the enhanced retention of issues-loaded solid nanoparticles after intra-articular administration. This retention 4 hours after injection was found to be 10.13%, which is almost a 16 fold higher than celecoxib in solution.

Morgen et al, *Pharm Res* (2013) 30:257-268 also used nanoparticles for improved local retention after intra-articular injection into the knee joint. These nanoparticles were cationic and it was demonstrated that a release of a conjugated peptide from these nanoparticles occurred at about 20% per week.

However, there is still a need in this art to deliver pharmaceutically active principles to joints in a mammal that retain the pharmaceutically active principle in the synovial area so that the drug is delivered over a longer period of time.

There is also a need in the art to provide a formulation in which the release rate of the at least one pharmaceutically active principle can be modulated by morselization of the formulation, which formulation is a biodegradable drug delivery composition.

There is also a need in the art to target pharmaceutically active principles directly to the synovial tissues and/or other joint tissues, including the synovial membrane and synovial fluid and the pharmaceutically active principle is retained in the synovial tissues.

In targeting the at least one active principle to synovial tissue and/or other joint tissues and morselizing, the release rate of the drug over time can be modulated over time.

These and other objects are achieved by the present invention as evidenced by the summary of the invention, the description of the preferred embodiments and the claims.

SUMMARY OF THE INVENTION

The present invention provides a method for morselizing a biodegradable drug delivery composition comprising at least one pharmaceutically active principle comprising:
(1) formulating a biodegradable drug composition comprising
(a) a biodegradable triblock copolymer having the formula:

$$PLA_v\text{-}PEG_w\text{-}PLA_x$$

wherein v and x are the number of repeat units ranging from 24 to 682 and w is the number of repeat units ranging from 4 to 273 and v=x or v≠x;
(b) a biodegradable diblock copolymer having the formula:

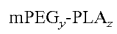

$$mPEG_y\text{-}PLA_z$$

wherein y and z are the number of repeat units with y ranging from 3 to 45 and z ranging from 7 to 327, wherein the ratio of the biodegradable triblock copolymer of (a) and the biodegradable diblock copolymer of (b) is 3:2 to 1:19 in said biodegradable drug composition; and (c) at least one pharmaceutically active principle;
(2) administering said formulated biodegradable drug delivery composition in at least one joint of a patient, such that it is contained within the articulating joint capsule.

In this method for morselizing the biodegradable drug delivery formulation is taken up by syringe for administration and injected into said at least one joint or manually formed in into a solid bolus by exposing the formulation to aqueous liquid and manual placement into the joint.

This method for morselizing causes the biodegradable drug delivery formulation to be subjected to a mechanical challenge such as those obtained by internal structures of the joints, articulation, weight bearing and/or by synovial fluid pressure. In this morselization method the biodegradable drug delivery formulation is broken into pieces.

In this morselization method the at least one pharmaceutically active principle is present in said biodegradable drug delivery formulation in an amount of 1% to 85% w %/w % and the polyethylene glycol chain in the triblock and the diblock ranges from 300 Da to 12 kDa.

In another aspect the polyethylene glycol chain in the triblock and the diblock is 2 kDa.

In one embodiment the polylactic repeat unit to ethylene oxide molar ratio is 1.6 to 7.2 in the triblock and 1.9 to 4.8 in the diblock and the degree of polymerization in the triblock is 72 to 324 and the degree of polymerization in the diblock is 85.5 to 216.

In one aspect the triblock is present in an amount of 6% to 24% (wt %/wt %) and the diblock is present in an amount of 12% to 40% (wt %/wt %).

In another embodiment the biodegradable drug delivery composition comprises mixing the triblock copolymer with the diblock copolymer in a biocompatible organic solvent to form a triblock copolymer and diblock copolymer mixture and adding to said triblock copolymer and diblock copolymer mixture at least one pharmaceutically active principle.

In another aspect in the method the solvent can be evaporated off.

In yet another aspect the triblock copolymer and diblock copolymer mixture and at least one pharmaceutically active principle is further exposed to an aqueous liquid to form a solid bolus.

In this method for morselizing, as described herein, the pieces of the biodegradable drug composition are broken down into smaller and smaller pieces. These pieces can range from about 1 centimeter down to 1 micron.

In another embodiment in the method for morselizing administration to the patient is 0.1 to 6 ml for the knee, 0.1 to 6 ml for the hip, 0.1 to 4 ml for the ankle, 0.1 to 6 ml for the shoulder and 0.1 to 2 ml for the elbow.

In another aspect, the at least one pharmaceutically active principle can be applied to post-surgical applications which can be, for example, total or partial knee replacements, total or partial hip replacements, total or partial ankle replacements, arthroscopic or open joint surgeries, microfracture, autologous chondrocyte implantation, mosaicplasty, debridement and lavage, ligament repair, tendon repair, rotator cuff repair, meniscus surgery, synovectomy or non-surgical applications by intra-articular injections for inflammatory disease or joint pain.

In yet another aspect the present invention provides a biodegradable drug delivery composition comprising at least one pharmaceutically active principle comprising:
(1) formulating a biodegradable drug composition comprising
(a) a biodegradable triblock copolymer having the formula:

$$PLA_v\text{-}PEG_w\text{-}PLA_x$$

wherein v and x are the number of repeat units ranging from 24 to 682 and w is the number of repeat units ranging from 4 to 273 and v=x or v≠x;
(b) a biodegradable diblock copolymer having the formula:

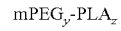

$$mPEG_y\text{-}PLA_z$$

wherein y and z are the number of repeat units with y ranging from 3 to 45 and z ranging from 7 to 327, wherein the ratio of the biodegradable triblock copolymer of (a) and the biodegradable diblock copolymer of (b) is 3:2 to 1:19 in said biodegradable drug composition; and (c) at least one pharmaceutically active principle for morselization of said biodegradable drug delivery composition; wherein said formulated biodegradable drug delivery composition is contained within the articulating joint capsule for morselization.

The present invention also provides a method for targeting at least one pharmaceutically active principle to synovial tissue said method comprising administering to a mammal or animal in need of such treatment a biodegradable drug delivery composition comprising:
(a) a biodegradable triblock copolymer having the formula:

$$A_v\text{-}B_w\text{-}A_x$$

wherein A is a polyester and B is polyethylene glycol and v and x are the number of repeat units ranging from 24 to 682 and w is the number of repeat units ranging from 4 to 273 and v=x or v≠x;
(b) a biodegradable diblock copolymer having the formula:

$$C_y\text{-}A_z$$

wherein A is a polyester and C is an end-capped polyethylene glycol and y and z are the number of repeat units with y ranging from 3 to 45 and z ranging from 7 to 327, wherein the ratio of the biodegradable triblock copolymer of (a) and the biodegradable CA diblock copolymer of (b) is 3:2 to 1:19 in said biodegradable drug composition; and (c) at least one pharmaceutically active principle.

In another aspect, the present invention provides a method for targeting at least one pharmaceutically active principle to synovial tissue said method comprising administering to a mammal or animal in need of such treatment a biodegradable drug delivery composition comprising (a) a biodegradable triblock copolymer having the formula:

$$A_v\text{-}B_w\text{-}A_x$$

wherein A is a polyester and B is polyethylene glycol and v and x are the number of repeat units ranging from 24 to 682 and w is the number of repeat units ranging from 4 to 273 and =x or v≠x;

(b) a biodegradable diblock copolymer having the formula:

$$C_y\text{-}A_z$$

wherein A is a polyester and C is an end-capped polyethylene glycol and y and z are the number of repeat units with y ranging from 3 to 45 and z ranging from 7 to 327, wherein the ratio of the biodegradable triblock copolymer of (a) and the biodegradable CA diblock copolymer of (b) is 1:3 to 1:9 in said biodegradable drug composition; and (c) at least one pharmaceutically active principle.

The present invention provides, in yet another aspect, a method for targeting at least one pharmaceutically active principle to synovial tissue said method comprising administering to a mammal or animal in need of such treatment a biodegradable drug delivery composition comprising (a) a biodegradable triblock copolymer having the formula:

$$A_v\text{-}B_w\text{-}A_x$$

wherein A is a polyester and B is polyethylene glycol and v and x are the number of repeat units ranging from 24 to 682 and w is the number of repeat units ranging from 4 to 273, v and x being ester repeat units and w being ethylene oxide repeat units and v=x or v≠x;

(b) a biodegradable diblock copolymer having the formula:

$$C_y\text{-}A_z$$

wherein A is a polyester and C is an end-capped polyethylene glycol and y and z are the number of repeat units with y ranging from 3 to 45 and z ranging from 7 to 327, y being the number of ethylene oxide repeat units and z the number of ester repeat units, wherein the ratio of the biodegradable triblock copolymer of (a) and the biodegradable CA diblock copolymer of (b) is 3:2 to 1:19 in said biodegradable drug composition; and (c) at least one pharmaceutically active principle.

In another aspect the present invention provides a method for targeting at least one pharmaceutically active principle to synovial tissue said method comprising administering to a mammal or animal in need of such treatment a biodegradable drug delivery composition comprising:

(a) a biodegradable triblock copolymer having the formula:

$$A_v\text{-}B_w\text{-}A_x$$

wherein A is a polyester and B is polyethylene glycol and v and x are the number of repeat units ranging from 24 to 682, and w is the number of repeat units ranging from 4 to 273, v and x being ester repeat units and w being ethylene oxide repeat units and v=x or v≠x;

(b) a biodegradable diblock copolymer having the formula:

$$C_y\text{-}A_z$$

wherein A is a polyester and C is an end-capped polyethylene glycol and y and z are the number of repeat units with y ranging from 3 to 45 and z ranging from 7 to 327, y being the number of ethylene oxide repeat units and z the number of lactyl or lactoyl repeat units, wherein the ratio of the biodegradable triblock copolymer of (a) and the biodegradable CA diblock copolymer of (b) is 1:3 to 1:9 in said biodegradable drug composition; and (c) at least one pharmaceutically active principle.

In another embodiment a method for targeting at least one pharmaceutically active principle to synovial tissue said method comprising administering to a mammal or animal in need of such treatment biodegradable drug delivery composition comprising:

(a) a biodegradable triblock copolymer having the formula:

$$PLA_v\text{-}PEG_w\text{-}PLA_x$$

wherein v and x are the number of repeat units ranging from 24 to 682 and w is the number of repeat units ranging from 4 to 273 and v=x or v≠x;

(b) a biodegradable diblock copolymer having the formula:

$$PEG_y\text{-}PLA_z$$

wherein y and z are the number of repeat units ranging from 3 to 237 or 3 to 371, wherein the ratio of the biodegradable triblock copolymer of (a) and the biodegradable diblock copolymer of (b) is 3:2 to 1:19 in said biodegradable drug composition and wherein the PEG in the diblock is end-capped; and (c) at least one pharmaceutically active principle.

A method for targeting at least one pharmaceutically active principle to synovial tissue said method comprising administering to a mammal or animal in need of such treatment biodegradable drug delivery composition comprising: (a) a biodegradable triblock copolymer having the formula:

$$PLA_v\text{-}PEG_w\text{-}PLA_x$$

wherein v and x are the number of repeat units ranging from 24 to 682 and w is the number of repeat units ranging from 4 to 273 and v=x or v≠x; (b) a biodegradable diblock copolymer having the formula:

$$PEG_y\text{-}PLA_z$$

wherein y and z are the number of repeat units with y ranging from 3 to 45 and z ranging from 7 to 327, wherein the ratio of the biodegradable triblock copolymer of (a) and the biodegradable diblock copolymer of (b) is 1:3 to 1:9 in said biodegradable drug composition and wherein the PEG in the diblock is end-capped; and (c) at least one pharmaceutically active principle, is yet another aspect of the present invention.

In yet another aspect a method for targeting at least one pharmaceutically active principle to synovial tissue said method comprising administering to a mammal or animal in need of such treatment biodegradable drug delivery composition is provided, which comprises: (a) a biodegradable triblock copolymer present in an amount of 2.0% to 45% (w %/w %) of the total composition having the formula:

wherein v and x are the number of repeat units ranging from 24 to 682 and w is the number of repeat units ranging from 4 to 273 and v=x or v≠x; (b) a biodegradable diblock copolymer present in an amount of 8.0% to 50% (w %/w %) of the total composition having the formula:

wherein y and z are the number of repeat units with y ranging from 3 to 45 and z ranging from 7 to 327, wherein the ratio of the biodegradable triblock copolymer of (a) and the biodegradable diblock copolymer of (b) is 3:2 to 1:19 in said biodegradable drug composition and wherein the PEG in the diblock is end capped and (c) at least one pharmaceutically active principle is present in an amount of 1% to 20% (w %/w %) of the total composition.

In yet another aspect a method for targeting a pharmaceutically active principle to synovial tissue said method comprising administering to a mammal or animal in need of such treatment biodegradable drug delivery composition is provided, which comprises: (a) a biodegradable triblock copolymer having the formula:

wherein v and x are the number of repeat units ranging from 24 to 682 and w is the number of repeat units ranging from 4 to 273 and v=x or v≠x;
(b) a biodegradable diblock copolymer present in an amount of having the formula:

wherein y and z are the number of repeat units ranging from 7 to 371, wherein the ratio of the biodegradable triblock copolymer of (a) and the biodegradable diblock copolymer of (b) is 1:3 to 1:9 in said biodegradable drug composition and wherein the PEG in the diblock is end capped, wherein the total polymer content ranging from 20% to 50% (w %/w %) of the total composition and (c) at least one pharmaceutically active principle is present in an amount of 10% to 20% (w %/w %) of the total composition.

In the method for targeting at least one pharmaceutically active principle to synovial tissue the biodegradable drug delivery compositions of the invention can have a lactic acid to ethylene oxide molar ratio in the composition of between 0.5 to 3.5 or 0.5 to 22.3 for the triblock copolymer and between 2 to 6 or 0.8 to 13 for the diblock copolymer.

In yet another aspect in the method for targeting a pharmaceutically active principle to synovial tissue the biodegradable drug delivery compositions of the invention can have a lactic acid to ethylene oxide molar ratio in the composition of between 0.5 to 2.5 for the triblock copolymer and between 3 to 5 for the diblock copolymer.

In one aspect the biodegradable drug delivery composition is an injectable liquid that when it is inserted into the intra-articular space becomes a hardened implant, which delivers the at least one pharmaceutically active principle over a prolonged duration.

In yet another aspect the biodegradable delivery drug composition can be used as a spatial formulation such that it can be applied onto or inside the intra-articular space of a mammal. For example, it can be dispensed during surgery to the intra-articular space to treat synovial tissue.

In another aspect, the at least one pharmaceutically active principle in this targeting method can be applied to post-surgical applications which can be, for example, total or partial knee replacements, total or partial hip replacements, total or partial ankle replacements, arthroscopic or open joint surgeries, microfracture, autologous chondrocyte implantation, mosaicplasty, debridement and lavage, ligament repair, tendon repair, rotator cuff repair, meniscus surgery, synovectomy or non-surgical applications by intra-articular injections for inflammatory disease or joint pain.

In another aspect the biodegradable drug composition is in the form of a solid rod implant that can be inserted into the joint. Besides solid rods, other shapes can be formulated and inserted into the body according to their medical applications.

Use of a biodegradable drug composition, as described herein, for targeting at least one pharmaceutically active principle to synovial tissue in a mammal or an animal is yet another aspect of the present invention.

Other aspects and embodiments are set forth below, or will readily arise from the following description of the preferred embodiments.

BRIEF DESCRIPTION OF THE DRAWINGS

The patent or application file contains at least one color drawing. Copies of this patent or patent application publication with color drawing will be provided by the USPTO upon request and payment of the necessary fee.

FIG. 5A-5C shows the morselization behaviour of each formulation of Example 9.

DESCRIPTION OF THE PREFERRED EMBODIMENTS

Figure 1:
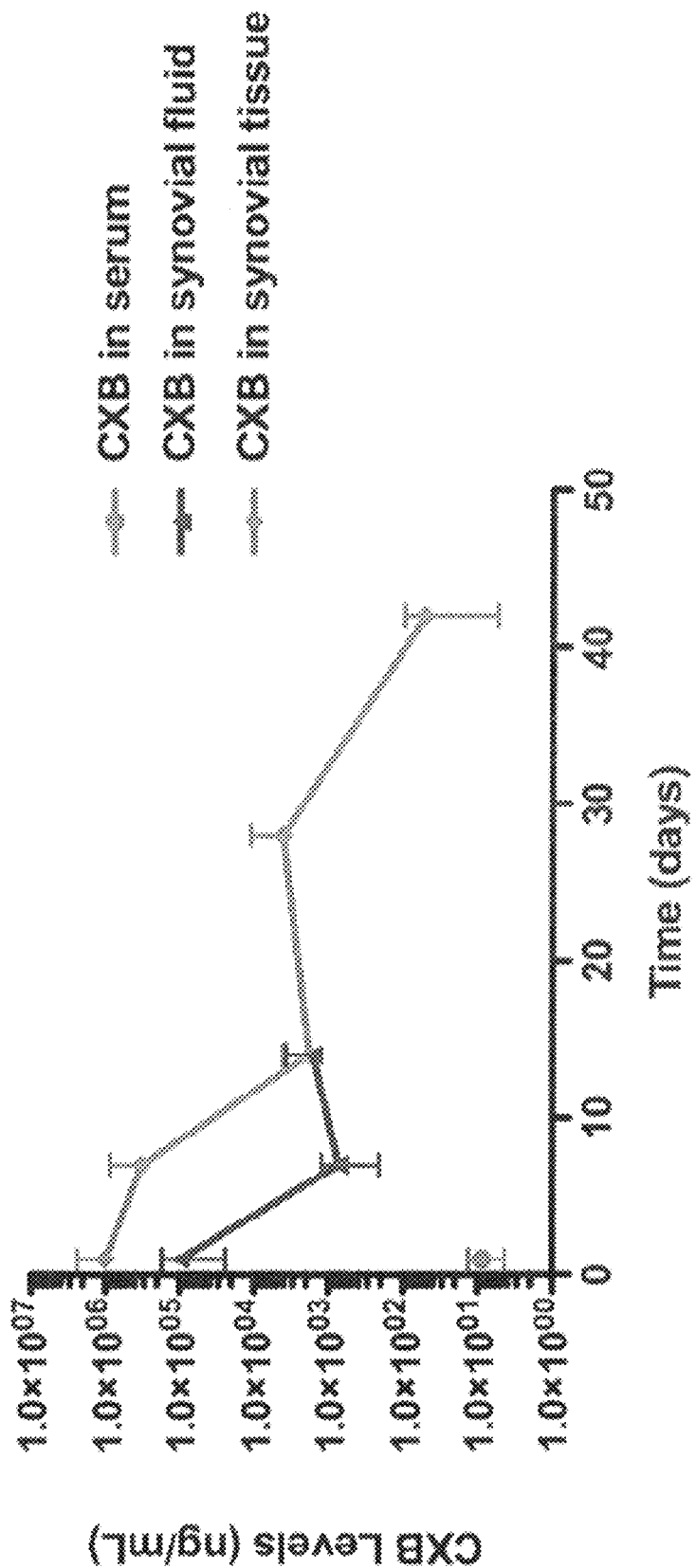
FIG. 1 is a graph demonstrating the in vivo quantitative pharmokinetics profiles of celecoxib delivery over time (days) to the synovial fluid, the synovial tissue and to serum.

As used herein the term "biodegradable" means that the triblock and diblock copolymers will after a period of time, erode, degrade or morselize in vivo to form smaller non-toxic components.

The term "animals" encompasses all members of the Kingdom Animalia.

Mammals, as used herein, encompasses any group of vertebrates the females of which have milk-secreting glands, including man. Examples of mammals include, but are not limited to cats, dogs, humans, pigs, horses, cattle, apes, chimpanzees and the like.

"Active principle" means a drug or medicine for treating various medical illnesses of the joints. Thus active principles, drugs and medicines are used interchangeably. The term drug or active principle as used herein includes without limitation physiologically or pharmacologically active substances that act locally or systemically in the body of an animal. At least one active principle is present in the biodegradable drug composition of the invention used in the method of the present invention. More than one active principle can be used in the methods of the present invention such as a non-steroidal anti-inflammatory drug and a local anaesthetic.

As used herein "disease" means any disorder in a mammal such as a human or animal caused by infection, diet, or by faulty functioning of a process.

The term "implant" means that the drug delivery compositions are injectable, are in situ forming and are biodegradable and turn into solid implants when injected into the intra-articular space. Thus, that the formulations that are synthesized are liquids such that they can be easily injected through a syringe without excessive force.

The term "spatial formulations" encompass any formulations that can be applied on or into the mammalian or animal body and do not necessarily have to be administered through a syringe.

As used herein "repeat units" are the fundamental recurring units of a polymer.

By "end-capped polyethylene glycol" (cPEG) refers to PEG's in which one terminal hydroxyl group is reacted and includes alkoxy-capped PEG's, urethane-capped PEG's ester-capped PEG's and like compounds. The capping group is a chemical group which does not contain a chemical function susceptible to react with cyclic esters like lactide, glycolactide, caprolactone and the like or other esters and mixtures thereof. The reaction of an end-capped PEG polymer with lactide generates a diblock cPEG-PLA copolymer.

As used herein polyethylene glycol, as abbreviated PEG throughout the application, is sometimes referred to as poly(ethylene oxide) or poly(oxyethylene) and the terms are used interchangeably in the present invention.

The abbreviation of "PLA" refers to poly(lactic acid).

The abbreviation of "PLGA" refers to poly(lactic-co-glycolic acid).

The abbreviation "T" or "TB" refers to a triblock copolymer(s), while the abbreviation "D" or "DB" refers to a diblock copolymer(s).

The term "diblock" as used herein refers, for example, to an end-capped PEG-polyester coplymer. "mPEG" refers to methoxy polyethylene glycol.

The term "triblock" refers, for example, to a polyester-PEG-polyester copolymer.

As used herein the term "synovial tissue" refers to the thin, loose vascular connective tissue that makes up, more specifically lines the interior of all joints and also the sheaths surrounding tendons such as in the hands and feet. Synovial tissue contains synovial cells, which secrete a viscous liquid called synovial fluid; this liquid contains proteins and hyaluronic acid and serves as a lubricant and nutrient for the joint cartilage surfaces.

"Synovial tissue conditions" means any disease that effects the synovial tissue or synovial fluid and can include any types of arthritis including osteoarthritis, rheumatoid arthritis, gout and rheumatic diseases including ankylosing sondylitis, fibromyalgia, infectious arthritis, juvenile idiopathic arthritis, lupus erythematosus, polymyalgia rheumatica, psoriatic arthritis, reactive arthritis and sclerodoma.

"Synovium," as used herein, is a membrane, also known as the synovial tissue, surrounding the joints that secretes a fluid that lubricates and provides nutrition to tissues.

As used herein "other joint tissues" include, but is not limited to articular cartilage, ligaments, meniscus, tendons, rotator cuffs and the like.

As used herein, "intra-articular" refers to the space inside of a joint between two bones, specifically to the portion of the joint contained by the joint capsule. Meaning "inside of a joint," intra-articular may refer to the space itself or, in the case of the body's movable joints, to any tissues or fluid found inside of the synovial membrane, the lining of the joint capsule. Within the synovial membrane is the synovial fluid, the lubricating fluid of the joint, as well as articular cartilage, which provides a near frictionless gliding surface or cushion between the adjoining bony surfaces. Other joint types may feature ligaments in their intra-articular space that hold the two bones together. In synovial or movable joints, these tissues are extra-articular, or outside of the joint capsule.

"Targeting," as used herein, means a method of delivering the at least one pharmaceutically active principle to a mammal or animal that increases the concentration of the drug(s) in the synovial tissue relative to other parts of the body. This targeting permits the prolongation and localization of the pharmaceutically active principle with the synovial tissue.

By "morselization" is meant the act of breaking up into fragments or particles; subdivision; decentralization. It is the same as morcellation. Morselization can be used to target joints, cartilage, ligaments, tendons, synovial fluid, rotator cuffs, meniscus, synovectomy or non-surgical applications by intra-articular injections for inflammatory disease or joint pain and the like.

Thus, in one aspect the present invention relates to a method for morselizing a biodegradable drug delivery composition comprising at least one pharmaceutically active principle comprising:

(1) formulating a biodegradable drug composition comprising
  (a) a biodegradable triblock copolymer having the formula:

$$PLA_v\text{-}PEG_w\text{-}PLA_x$$

wherein v and x are the number of repeat units ranging from 24 to 682 and w is the number of repeat units ranging from 4 to 273 and v=x or v≠x;
(b) a biodegradable diblock copolymer having the formula:

$$mPEG_y\text{-}PLA_z$$

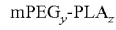

wherein y and z are the number of repeat units with y ranging from 3 to 45 and z ranging from 7 to 327, wherein the ratio of the biodegradable triblock copolymer of (a) and the biodegradable diblock copolymer of (b) is 3:2 to 1:19 in said biodegradable drug composition; and (c) at least one pharmaceutically active principle;

(2) administering said formulated biodegradable drug delivery composition in at least one joint of a patient, such that it is contained within the articulating joint capsule.

In said method of morselization the formulated biodegradable drug delivery composition can be taken up by a syringe for administration and injected into said joint or manually formed in into a solid bolus by exposing the formulated biodegradable drug delivery to an aqueous liquid and manually placed into the joint or joints. In this latter system of delivery, the biodegradable drug delivery composition can be shaped according to the area of the joint in which it is placed. Thus the size and shape may differ depending on the type of joint.

When administered to the joint, the biodegradable drug composition can be subjected to a mechanical challenge via internal structures of the joints, articulation, weight bearing and/or by synovial fluid pressure. This mechanical challenge is believed to aid in the morselization of the biodegradable drug composition. In this morselization process the biodegradable drug delivery composition is broken into pieces. These pieces can further degrade over time and can be broken down into smaller and smaller pieces. These smaller pieces can range from 1 centimeter down to 1 millimeter and further down to 1 micron. The pieces can be broken down over time.

The at least one pharmaceutically active principle (API) can be present in biodegradable drug delivery composition in an amount of 1% to 85% w %/w %. In another aspect the at least one API can be present in the biodegradable drug composition in an amount of 1% to 40% w %/w % In another aspect the at least one API can be present in the biodegradable drug composition in an amount of 5% to 40% w %/w %. In another aspect the at least one API can be present in the biodegradable drug composition in an amount of 5% to 15% w %/0/w %. In yet another aspect the at least one API can be present in the biodegradable drug composition in an amount of 5% to 30% w %/w %.

The at least one pharmaceutically active principle that can be used in the present biodegradable drug delivery composition include anti-oxidant agents such as alkyl gallates, butylated hydroxyanisole (BHA), butylated hydroxytoluene (BHT), alpha-tocopherol, ascorbic acid, polyphenols, flavonoids, beta-carotene, vitamin A, vitamin C, vitamin E, lipoic acid, dithiolethione, ovothiol, glutathione, selenium, quercetin, melatonin, sodium sulfite, sodium bisulfite, sodium metabisulfite, thiogly colic acid, monothioglycerol, L-cysteine or a combination thereof.

Anti-infective agents are agents that inhibit infection and include anti-viral agents, anti-fungal agents and antibiotics.

Anti-viral Agents, which are agents that inhibit virus, and include vidarabine, acyclovir and trifluorothymidine.

Anti-fungal agents, which are agents that inhibit fungal growth. Anti-fungal agents include amphoterecin B, myconazole, terconazole, econazole, isoconazole, thioconazole, biphonazole, clotrimazole, ketoconazole, butaconazole, itraconazole, oxiconazole, phenticonazole, nystatin, naphthyphene, zinoconazole, cyclopyroxolamine and fluconazole.

Major classes of antibiotics are (1) the beta-lactams, including the penicillins, cephalosporins and monobactams; (2) the aminoglycosides, e.g. gentamicin, tobramycin, netilmycin, and amikacin; (3) the tetracyclines; (4) the sulfonamides and trimethoprim; (5) the fluoroquinolones, e.g. ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides.

Numerous drugs fall into the category of chemotherapeutic agents useful in the treatment of neoplastic disease. Such agents can include antimetabolites such as metotrexate (folic acid derivatives), fluoroaucil, cytarabine, mercaptopurine, thioguanine, petostatin (pyrimidine and purine analogs or inhibitors), a variety of natural products such as vincristine and vinblastine (vinca alkaloid), etoposide and teniposide, various antibiotics such as miotomycin, plicamycin, bleomycin, doxorubicin, danorubicin, dactomycin; a variety of biological response modifiers including interferon-alpha; a variety of miscellaneous agents and hormonal modulators including cisplatin, hydroxyurea, mitoxantorne, procarbozine, aminogultethimide, prednisone, progestins, estrogens, antiestorgens such as tamoxifen, androgenic steroids, antiadrogenic agents such as flutamide, gonadotropin releasing hormones analogs such as leuprolide, the matrix metalloprotease inhibitors (MMPIs) as well as anti-cancer agents including Taxol (paclitaxel) and related molecules collectively termed taxoids, taxines or taxanes.

Anti-nociceptive agents such as Anti-NGF, Autotaxin inhibitors/LPA receptor antagonists, TRPV1 Antagonists, Nav1.7 Antagonists and Resolvins.

NSAID, non COX-2 or COX-2 specific such as COX-2 inhibitors, mPEGS-1 inhibitors, EP4-receptor antagonists, etofenamate, celecoxib, apricoxib, rofecoxib, nabumetone, benorilate, etoricoxib, ampiroxicam, aminophemazone, valdecoxib, acetominophen, bufexamac, nimesulide, parecoxib, mefenamic acid, dexibuprofen, ibuprofen, flurbiprofen, aspirin, dexdetoprofen, diclofenac, diflunisal, etodolac, fenoprofen, firocoxib, flurbiprofen, indomethacin, ketoprofen, ketorolac, lornoxicam, loxoprofen, loxomac, lumiracoxib, meclofenamic acid, meloxicam, naproxen, naprosyn, nimalox, oxaporozin, piroxicam, salsalate, sulindac, tenoxicam, tolfenamic acid and mixtures thereof.

DMOAD such as HIF2a inhibitor, complement cascade regulators, TGF beta signalling modulators, zinc transporter, agrecanase inhibitors and EP4-receptor antagonists.

Anabolic agents such as FGF-18 and OP-1.

Anti-catabolics agents such as lubricin, TIMP-3, OP-1, MMP-13 inhibitor, cathepsin K, anti-cytokine agents (e.g. anti-IL-β and TNFα blockers.

Autophagy regulators such as mTOR inhibitors and sinomenium.

Anti-osteoclast-mediated bone loss agents such as oestrogens, selective oestrogen receptor modifiers (SERMs), bisphosphonates (e.g. zoledronate), strontium ranelate, calcitonin and parathyroid hormone.

Nutraceutical agents such as glucosamine and chondroitin sulfate.

Local anesthetics agents such as bupivacaine, mepivicaine, articaine, ropivacaine, dibucaine, etidocaine, tetracaine, lidocaine, xylocalne, and the like including mixtures and/or salts and/or derivatives thereof.

Biologics such as anti-NGF (Tanezumab) and FGF18 (sprifermin).

Mixtures of the at least one APIs, as described herein, can also be administered. This mixture depends on the symptoms of the patient in the at least one joint that must be treated.

In the method for morselizing, as described herein, the polyethylene glycol chain in the triblock and the diblock can range from 300 Da to 12 kDa. In another aspect, the polyethylene glycol chain in the triblock and the diblock can range from 5 kDa to 8 kDa. In yet another aspect the polyethylene glycol chain in the triblock and the diblock can range from 1 kDa to 5 kDa. In still yet another aspect the polyethylene glycol chain in the triblock and the diblock can range from 1 kDa to 2 kDa. In yet another aspect, the polyethylene glycol chain in the triblock is 2 kDA and the diblock is 1 kDa. In still yet another aspect the polyethylene glycol chain in the triblock is 1 kDa and the diblock is 2 kDa. In still yet another aspect the polyethylene glycol chain in the triblock is 2 kDa and the diblock is 2 kDa.

In the method for morselizing, as described herein, the polylactic repeat unit to ethylene oxide molar ratio can range from 1.6 to 7.2 in the triblock and 1.9 to 4.8 in the diblock. In another aspect the polylactic repeat unit to ethylene oxide molar ratio can range from 2.0 to 6.0 in the triblock and 2.0 to 3.0 in the diblock. In yet another aspect the polylactic repeat unit to ethylene oxide molar ratio can range from 3.0 to 6.5 in the triblock and 2.5 to 4.5 in the diblock.

The degree of polymerization, in the morselization method described herein, can range from 72 to 324 in the triblock and the degree of polymerization in the diblock can range from 85.5 to 216. In another aspect the degree of polymerization, in the morselization method described herein, can range from 92 to 135 in the triblock and the degree of polymerization in the diblock can range from 91 to 180. In yet another aspect the degree of polymerization, in the morselization method described herein, can range from 95 to 130 in the triblock and the degree of polymerization in the diblock can range from 95 to 175. In another aspect the degree of polymerization, in the morselization method described herein, can range from 98 to 132 in the triblock and the degree of polymerization in the diblock can range from 95 to 175.

In the method for morselizing, as described herein, the triblock can be present in an amount of 6% to 24% (wt %/wt %) and the diblock can be present in an amount of 12% to 40% (wt %/wt %) in the biodegradable drug composition. In the method for morselizing, as described herein, the triblock can be present in an amount of 5% to 30% (wt %/wt %) and the diblock can be present in an amount of 15% to 25% (wt %/wt %) in the biodegradable drug composition. In the method for morselizing, as described herein, the triblock can be present in an amount of 10% to 40% (wt %/wt %) and the diblock can be present in an amount of 10% to 20% (wt %/wt %) in the biodegradable drug composition. In the method for morselizing, as described herein, the triblock can be present in an amount of 15% to 50% (wt %/wt %) and the diblock can be present in an amount of 5% to 35% (wt %/wt %) in the biodegradable drug composition.

In the method for morselizing, as described herein, the formulation of said biodegradable drug composition comprises mixing the triblock copolymer with the diblock copolymer in a biocompatible organic solvent to form a triblock copolymer and diblock copolymer mixture. The at least one pharmaceutically active principle is then added to said triblock copolymer and diblock copolymer mixture. The solvent can be evaporated off.

In administering to a patient the amounts used can be about 0.1 to 6 ml for the knee, about 0.1 to 6 ml for the hip, about 0.1 to 4 ml for the ankle, about 0.1 to 6 ml for the shoulder and about 0.1 to 2 ml for the elbow.

In another aspect, the at least one pharmaceutically active principle can be applied to post-surgical applications which can be, for example, total or partial knee replacements, total or partial hip replacements, total or partial ankle replacements, arthroscopic or open joint surgeries, microfracture, autologous chondrocyte implantation, mosaicplasty, debridement and lavage, ligament repair, tendon repair, rotator cuff repair, meniscus surgery, synovectomy or non-surgical applications by intra-articular injections for inflammatory disease or joint pain.

In yet another embodiment a biodegradable drug delivery composition is described comprising at least one pharmaceutically active principle comprising:

(1) formulating a biodegradable drug composition comprising
(a) a biodegradable triblock copolymer having the formula:

$PLA_v$-$PEG_w$-$PLA_x$ wherein v and x are the number of repeat units ranging from 24 to 682 and w is the number of repeat units ranging from 4 to 273 and v=x or v≠x;
(b) a biodegradable diblock copolymer having the formula:

$mPEG_y$-$PLA_z$ wherein y and z are the number of repeat units with y ranging from 3 to 45 and z ranging from 7 to 327, wherein the ratio of the biodegradable triblock copolymer of (a) and the biodegradable diblock copolymer of (b) is 3:2 to 1:19 in said biodegradable drug composition; and (c) at least one pharmaceutically active principle for morselization of said biodegradable drug delivery composition;
wherein said formulated biodegradable drug delivery is contained within the articulating joint capsule for morselization.

The present invention also relates to a method for targeting at least one pharmaceutically active principle to synovial tissue said method comprising administering to a mammal or animal in need of such treatment a biodegradable drug delivery composition comprising:

(a) a biodegradable triblock copolymer having the formula:

$A_v$-$B_w$-$A_x$ wherein A is a polyester and B is polyethylene glycol and v and x are the number of repeat units ranging from 24 to 682 and w is the number of repeat units ranging from 4 to 273 and v=x or v≠x;
(b) a biodegradable diblock copolymer having the formula:

$C_y$-$A_z$ wherein A is a polyester and C is an end-capped polyethylene glycol and y and z are the number of repeat units with y ranging from 3 to 45 and z ranging from 7 to 327, wherein the ratio of the biodegradable triblock copolymer of (a) and the biodegradable diblock copolymer of (b) is 3:2 to 1:19 in said biodegradable drug composition; and (c) at least one pharmaceutically active principle.

The number of repeat units of v, w and x in the triblock composition may vary due to the targeted time of release of the active principle and the type of active principle itself. Therefore the number of repeat units in the triblock of v, w and x can range from 8 to 1090, from 10 to 850, from 20 to 700, from 30 to 650 and v=x or v≠x. For instance, w can be 273, while x+y can be 682 and v=x or v≠x or w can be 136 and x+y can be 273 and v=x or v≠x or w can be 45.5 and x+y can be 546 or w can be 273 and x+y can be 136.

The size of the PEG in the triblock can range from 194 Da to 12,000 Da. The size of the PEG in the triblock and diblock can also range from 164 Da to 12 kDa.

The polyester in the triblock can be polylactic acid (PLA), polycaprolactone (PCL), polyglycolic acid (PGA) or polyhydroxyalkanoate (PHA). In one embodiment the polyester that is used is polylactic acid.

The degree of polymerization for DP-PEG is calculated by dividing the PEG molecular weight by the EO unit molecular weight (44 Da). v+x equals the degree of polymerization (number of repeat units) for PLA. DP-PLA is calculated by multiplying DP-PEG by the LA/EO ratio.

The triblock copolymer is then combined with a biodegradable diblock copolymer having the formula: $C_y$-$A_z$, wherein A is a polyester and C is an end-capped polyethylene glycol and y and z are the number of repeat units ranging from 7 to 371 or from 3 to 327. This combination has a ratio of triblock copolymer to diblock copolymer ranging from 3:2 to 1:19 or 1:3 to 1:9.

Examples of end-capped polyethylene glycols include alkoxy capped PEG's such as methoxyPEG or ethoxyPEG, urethane-capped PEG's, ester-capped PEG's, amine-capped PEG's and amide-capped PEG's. This list of end-capped PEG's is not exhaustive and a person skilled in the art would recognize additional end-capped PEG's, which are not listed.

However the number of repeat units (degree of polymerization (DP)) of y and z in the diblock composition may also vary. Thus, y can, for example, range from 7 to 43 or 3 to 45 and z can range from 32 to 123 or 7 to 327. For example, y can be 25 and z can be 123, y can be 34.5 and z can be 123 or y can be 45 and z can be 32. The degree of polymerization for DP-PEG is calculated by dividing the PEG molecular weight of the capped PEG by the EO unit molecular weight (44 Da). The DP-PLA is calculated by multiplying DP-PEG by the LA/EO ratio.

The polyester in the diblock can be polylactic acid (PLA), polycaprolactone (PCL), polyglycolic acid (PGA), poly(lactic-co-glycolic acid) (PLGA) or polyhydroxyalkanoate (PHA). In one embodiment the polyester that is used is polylactic acid. In another embodiment the polyester is poly(lactic-co-glycolic acid).

The LA/EO ratio refers to the molar ratio of lactic acid units to ethylene oxide units that is present in the biodegradable drug delivery composition. It is determined experimentally by NMR. The LA/EO molar ratio of the combined triblock copolymer can range from 0.5 to 3.5. In another aspect the LA/EO molar ratio in the triblock can range from 0.5 to 2.5 in the biodegradable drug delivery composition described herein. In yet another aspect the LA/EO ratio in the triblock can range from 0.5 to 22.3.

The LA/EO ratio in the diblock can range from 2 to 6. In another aspect the LA/EO ratio in the diblock can range from 3 to 5 in the biodegradable drug delivery composition. In another aspect the LA/EO ratio in the diblock can range from 0.8 to 13.

The degree of polymerization or DP is the number of repeat units in an average polymer chain at time t in a polymerization reaction. For example, the degree of polymerization for PEG is about 45 to 170 or it can be 4 to 273 or 3 to 45, while for PLA it can range from about 84 to 327 or it can be 24 to 682 or 7 to 327.

In another aspect, the present invention provides a method for targeting at least one pharmaceutically active principle to synovial tissue said method comprising administering to a mammal or animal in need of such treatment a biodegradable drug delivery composition comprising
(a) a biodegradable triblock copolymer having the formula:

$A_v\text{-}B_w\text{-}A_x$ wherein A is a polyester and B is polyethylene glycol and v and x are the number of repeat units ranging from 24 to 682 and w is the number of repeat units ranging from 4 to 273 and =x or v≠x;
(b) a biodegradable diblock copolymer having the formula:

$C_y\text{-}A_z$ wherein A is a polyester and C is an end-capped polyethylene glycol and y and z are the number of repeat units with y ranging from 3 to 45 and z ranging from 7 to 327, wherein the ratio of the biodegradable triblock copolymer of (a) and the biodegradable diblock copolymer of (b) is 1:3 to 1:9 in said biodegradable drug composition; and (c) at least one pharmaceutically active principle.

The present invention provides, in yet another aspect, a method for targeting at least one pharmaceutically active principle to synovial tissue said method comprising administering to a mammal or animal in need of such treatment a biodegradable drug delivery composition comprising
(a) a biodegradable triblock copolymer having the formula:

$A_v\text{-}B_w\text{-}A_x$ wherein A is a polyester and B is polyethylene glycol and v and x are the number of repeat units ranging from 24 to 682 and w is the number of repeat units ranging from 4 to 273 v and x being ester repeat units and w being ethylene oxide repeat units and v=x or v≠x;
(b) a biodegradable diblock copolymer having the formula:

$C_y\text{-}A_z$ wherein A is a polyester and C is an end-capped polyethylene glycol and y and z are the number of repeat units with y ranging from 3 to 45 and z ranging from 7 to 327, y being the number of ethylene oxide repeat units and z the number of ester repeat units, wherein the ratio of the biodegradable triblock copolymer of (a) and the biodegradable CA diblock copolymer of (b) is 3:2 to 1:19 in said biodegradable drug composition; and
(c) at least one pharmaceutically active principle.

In another aspect the present invention provides a method for targeting at least one pharmaceutically active principle to synovial tissue said method comprising administering to a mammal or animal in need of such treatment a biodegradable drug delivery composition comprising:
(a) a biodegradable triblock copolymer having the formula:

$A_v\text{-}B_w\text{-}A_x$ wherein A is a polyester and B is polyethylene glycol and v and x are the number of repeat units ranging from 24 to 682, and w is the number of repeat units ranging from 4 to 273, v and x being ester repeat units and w being ethylene oxide repeat units and v=x or v≠x;
(b) a biodegradable diblock copolymer having the formula:

$C_y\text{-}A_z$ wherein A is a polyester and C is an end-capped polyethylene glycol and y and z are the number of repeat units with y ranging from 3 to 45 and z ranging from 7 to 327, y being the number of ethylene oxide repeat units and z the number of ester repeat units, wherein the ratio of the biodegradable triblock copolymer of (a) and the biodegradable CA diblock copolymer of (b) is 1:3 to 1:9 in said biodegradable drug composition; and
(c) at least one pharmaceutically active principle.

In another embodiment a method for targeting at least one pharmaceutically active principle to synovial tissue said method comprising administering to a mammal or animal in need of such treatment biodegradable drug delivery composition comprising:
(a) a biodegradable triblock copolymer having the formula:

$PLA_v\text{-}PEG_w\text{-}PLA_x$ wherein v and x are the number of repeat units ranging from 24 to 682 and w is the number of repeat units ranging from 4 to 273 and v=x or v≠x;
(b) a biodegradable diblock copolymer having the formula:

$PEG_y\text{-}PLA_z$ wherein y and z are the number of repeat units ranging from 3 to 237 or 3 to 371, wherein the ratio of the biodegradable triblock copolymer of (a) and the biodegradable diblock copolymer of (b) is 3:2 to 1:19 in said biodegradable drug composition and wherein the PEG in the diblock is end-capped; and (c) at least one pharmaceutically active principle.

A method for targeting at least one pharmaceutically active principle to synovial tissue said method comprising administering to a mammal or animal in need of such treatment biodegradable drug delivery composition comprising: (a) a biodegradable triblock copolymer having the formula:

$PLA_v\text{-}PEG_w\text{-}PLA_x$ wherein v and x are the number of repeat units ranging from 24 to 682 and w is the number of repeat units ranging from 4 to 273 and v=x or v≠x;

(b) a biodegradable diblock copolymer having the formula:

$PEG_y\text{-}PLA_z$ wherein y and z are the number of repeat units with y ranging from 3 to 45 and z ranging from 7 to 327, wherein the ratio of the biodegradable triblock copolymer of (a) and the biodegradable diblock copolymer of (b) is 1:3 to 1:9 in said biodegradable drug composition and wherein the PEG in the diblock is end-capped; and (c) at least one pharmaceutically active principle, is yet another aspect of the present invention.

In yet another aspect a method for targeting at least one pharmaceutically active principle to synovial tissue said method comprising administering to a mammal or animal in need of such treatment biodegradable drug delivery composition is provided, which comprises:

(a) a biodegradable triblock copolymer present in an amount of 2.0% to 45% (w %/w %) of the total composition having the formula:

$PLA_v\text{-}PEG_w\text{-}PLA_x$ wherein v and x are the number of repeat units ranging from 24 to 682 and w is the number of repeat units ranging from 4 to 273 and v=x or v≠x; (b) a biodegradable diblock copolymer present in an amount of 8.0% to 50% (w %/w %) of the total composition having the formula:

$PEG_y\text{-}PLA_z$ wherein y and z are the number of repeat units with y ranging from 3 to 45 and z ranging from 7 to 327, wherein the ratio of the biodegradable triblock copolymer of (a) and the biodegradable diblock copolymer of (b) is 3:2 to 1:19 in said biodegradable drug composition and wherein the PEG in the diblock is end capped and (c) at least one pharmaceutically active principle is present in an amount of 1% to 20% (w %/w %) of the total composition.

In yet another aspect a method for targeting at least one pharmaceutically active principle to synovial tissue said method comprising administering to a mammal or animal in need of such treatment biodegradable drug delivery composition is provided, which comprises: (a) a biodegradable triblock copolymer having the formula:

$PLA_v\text{-}PEG_w\text{-}PLA_x$ wherein v and x are the number of repeat units ranging from 24 to 682 and w is the number of repeat units ranging from 4 to 273 and v=x or v≠x;

(b) a biodegradable diblock copolymer present in an amount of having the formula:

$PEG_y\text{-}PLA_z$ wherein y and z are the number of repeat units ranging from 7 to 371, wherein the ratio of the biodegradable triblock copolymer of (a) and the biodegradable diblock copolymer of (b) is 1:3 to 1:9 in said biodegradable drug composition and wherein the PEG in the diblock is end capped wherein the total polymer content ranges from 20% to 50% (w %/w %) of the total composition or 30% to 50% (w %/w %) of the total composition and (c) at least one pharmaceutically active principle is present in an amount of 10% to 20% (w %/w %) of the total composition.

In the method for targeting the at least one pharmaceutically active principle to synovial tissue the biodegradable drug delivery compositions of the invention can have a lactic acid to ethylene oxide molar ratio in the composition of between 0.5 to 3.5 or 0.5 to 22.3 for the triblock copolymer and between 2 to 6 or 0.8 to 13 for the diblock copolymer.

In yet another aspect in the method for targeting a pharmaceutically active principle to synovial tissue the biodegradable drug delivery compositions of the invention can have a lactic acid to ethylene oxide molar ratio in the composition of between 0.5 to 2.5 for the triblock copolymer and between 3 to 5 for the diblock copolymer.

In one aspect the biodegradable drug delivery composition in this method for targeting is an injectable liquid that when it is inserted into the intra-articular space becomes a hardened implant.

In yet another aspect the biodegradable delivery drug composition can be used in this method for targeting as a spatial formulation such that it can be applied onto or inside the intra-articular space of a mammal or animal. For example, it can be dispensed during surgery to the intra-articular space to treat synovial tissue.

In another aspect the biodegradable drug composition in this method for targeting is in the form of a rod implant or a solid implant of any shape that can be inserted into the body.

The ratio of the biodegradable triblock copolymer of (a) and the biodegradable CA diblock copolymer of (b) is 3:2 to 1:19 in said biodegradable drug composition for targeting. In one embodiment the ratio of the biodegradable triblock copolymer of and the biodegradable diblock copolymer is selected from the group of 1:3 to 1:9.

The length of the polyester chain in this method for targeting is defined by its polyester to ethylene oxide molar ratio, which is between 0.5 to 3.5 or 0.5 to 2.5 or 0.5 to 22.3 for the triblock copolymer and 3 to 5 or 2 to 6 or 0.8 to 13 for the diblock copolymer. Thus, for example, if polylactic acid is used the chain length is defined by the lactic acid/ethylene oxide molar ratio. Similarly if polyglycolic acid is used, the chain length is defined by the polyglycolic acid/ethylene oxide molar ratio or the polycaprolactone/ethylene oxide molar ratio or the polyhydroxyalkanoate/ethylene oxide molar ratio. If poly(lactic-co-glycolic) acid is used the chain length is defined by the ratio of LA+G/EO.

The mass of the end-capped polyethylene glycol in this method for targeting can range from 164 Da to 2 kDa or from 100 Da to 2 kDa. It can range in the lower 100 to 300 Da range or in the 1 kDa to 2 kDa range.

The size of the polyethylene glycol chain in this method for targeting ranges from 200 Da to 12 kDa in the biodegradable drug delivery composition or it can range from 200 Da to 12 kDa or 194 Da to 12 kDa.

The polymers in this method for targeting are present in an amount of 20% to 50% (w %/w %) of the total weight of the composition. In another aspect the total weight of the polymers present in the biodegradable drug composition is 30% to 50% (w %/w %) of the total weight of the composition. In yet another aspect the polymers are present in the biodegradable drug composition at 40% to 50% (w %/w %) of the total weight of the composition.

Thus, the triblock copolymer is present in an amount of 3.0% to 45% (w %/w %) of the total weight of the composition in this method for targeting. In another aspect the triblock copolymer is present in an amount of 6% to 10% (w %/w %) of the total weight of the composition. In yet another aspect the triblock copolymer is present in an amount of 20% to 40% (w %/w %) of the total weight of the composition.

Likewise the diblock copolymer can be present in the biodegradable drug composition in this method for targeting in an amount of 8% to 50% (w %/w %) of the total weight of the composition. In another aspect the diblock copolymer is present in an amount of 10% to 20% (w %/w %) of the total weight of the composition. In yet another aspect the diblock copolymer is present in an amount of 20% to 40% (w %/w %) of the total weight of the composition.

The at least one pharmaceutically active principle in this method for targeting is entrapped in the triblock:diblock biodegradable drug delivery composition. Representative drugs and biologically active agents to be used in the invention include, without limitation, any pharmaceutically active principle that can be used to treat any medical conditions of the synovial tissues including peptide drugs, protein drugs, desensitizing agents, antigens, non-steroidal anti-inflammatory agents, anti-inflammatory drugs, anaesthetics, corticosteroids, analgesics and the like. Examples of non-steroidal anti-inflammatory agents include etofenamate, celecoxib, apricoxib, rofecoxib, nabumetone, benorilate, etoricoxib, ampiroxicam, aminophemazone, valdecoxib, acetominophen, bufexamac, nimesulide, parecoxib, mefenamic acid, dexibuprofen, ibuprofen, flurbiprofen, aspirin, dexdetoprofen, diclofenac, diflunisal, etodolac, fenoprofen, firocoxib, flurbiprofen, indomethacin, ketoprofen, ketorolac, lornoxicam, loxoprofen, loxomac, lumiracoxib, meclofenamic acid, meloxicam, naproxen, naprosyn, nimalox, oxaporozin, piroxicam, salsalate, sulindac, tenoxicam, tolfenamic acid and mixtures thereof.

Thus combinations of drugs can also be used in the biodegradable drug delivery composition of this invention for targeting synovial tissue. For instance, if one needs to treat osteoarthritis non-steroidal anti-inflammatory agents and corticosteroides can be administered together in the present invention.

Veterinary medicaments such as medicines for the targeting of synovial tissue for animals also form a part of the present invention.

To those skilled in the art, other drugs or biologically active agents that can be released in an aqueous environment can be utilized in the described delivery system. Also, various forms of the drugs or biologically active agents may be used. These include without limitation forms such as uncharged molecules, molecular complexes, salts, ethers, esters, amides, etc., which are biologically activated when injected into the animal or used as a spatial formulation such that it can be applied on or inside the body of an animal or as a rod implant.

The pharmaceutically effective amount of an active principle may vary depending on the active principle, the extent of the animal's medical condition and the time required to deliver the active principle. There is no critical upper limit on the amount of active principle incorporated into the polymer solution except for that of an acceptable solution or dispersion viscosity for injection through a syringe needle and that it can effectively treat the medical condition without subjecting the animal or plant to an overdose. The lower limit of the active principle incorporated into the delivery system is dependent simply upon the activity of the active principle and the length of time needed for treatment.

For instance some active principles may be present in the biodegradable drug delivery composition from 10 to 200 mg/gram. In another aspect the drugs should be present in the amount of 10 to 40 µg/gram. For a small molecule, for instance, the active principle can be loaded as high as 100 to 200 mg per gram.

Generally, the pharmaceutically active principle in this method for targeting is present in an amount of 1% to 20% (w %/w %) of the total weight of the composition. In another aspect the active principle is present in 1% to 4% (w %/w %) of the total weight of the composition. In another aspect the active principle is present in 2% to 4% (w %/w %) of the total weight of the composition. In yet another aspect the active principle, which is a small molecule, is present in an amount of 10% to 20% (w %/w %) of the total weight of the composition or 21% to 50% (w %/w %) of the total composition.

In the biodegradable drug delivery composition of the present invention, in this method for targeting, the pharmaceutically effective amount can be released gradually over an extended period of time. This slow release can be continuous or discontinuous, linear or non-linear and can vary due to the composition of the triblock copolymer and diblock copolymer. Thus, the higher the lactic acid content of the triblock and diblock copolymers in comparison with the polyethylene glycol content, as well as the amount of triblock and diblock copolymers present in the biodegradable drug composition the longer the release of the active principle or drug. In other words, the higher the LA/EO molar ratio and the greater weight percentage of the triblock and diblock copolymers, the longer it will take for the active principle to be released from the drug composition.

The active principle can be released for a duration of between 24 hours to 1 year or 7 days to 1 year or longer depending upon the type of treatment needed and the biodegradable drug delivery composition used. In one aspect the biodegradable drug delivery composition can deliver the active principle for at least 7 days. In another aspect the biodegradable drug delivery composition can deliver the active principle for at least 30 days. In one aspect the biodegradable drug delivery composition can deliver the active principle for at least 90 days. In yet another aspect the biodegradable drug delivery composition can deliver an active principle for 1 year or longer.

The biodegradable drug delivery composition in this method for targeting can be an injectable liquid at room temperature and be injected through a syringe without excessive force. But these biodegradable drug delivery compositions are also in situ forming and biodegradable and turn into solid implants or depots when injected into the animal or plant. Alternatively the biodegradable drug composition is produced as a solid, prepared as small particles and used as a powder which is sprinkled on the injured site. In another aspect the drug delivery composition is a rod implant, which can be implanted under the skin or in another compartment in the body.

In another aspect the drug delivery composition can be prepared and applied as a film. In yet another aspect the biodegradable delivery drug composition can be used as a spatial formulation such that it can be applied onto or inside the body of an animal.

The biodegradable drug delivery composition can further comprise a pharmaceutically acceptable carrier, adjuvant or vehicle. An acceptable carrier can be saline, buffered saline and the like. It can be added to the biodegradable drug delivery composition after its formulation with the drug and diblock copolymer and triblock copolymer.

The adjuvant can be formulated simultaneously when mixing the drug. In this regard the adjuvants that can be used are alum, aluminum phosphate, calcium phosphate, MPL™, CpG motifs, modified toxins, saponins, endogenous stimulatory adjuvants such as cytokines, Freunds complete and incomplete adjuvants, ISCOM type adjuvants, muramyl peptides and the like.

The vehicle can be any diluent, additional solvent, filler or binder that may alter the delivery of the active principle when needed in the biodegradable drug delivery composition. Examples include small amounts of triglycerides such as triacetin or tripropionin. The amount that can be used in the present method in the biodegradable drug delivery compositions of the present invention can vary from 12% to 20% (w %/w %). In one aspect, a triacetin can be added in the formulation at 17.0% (w %/w %). In another aspect tripropionin (abbreviated herein as Tripro) can be added at 16% (w %/w %).

The organic solvent that can be used in the method for the solubilization of the triblock copolymer or diblock copolymer is selected from the group of: benzyl alcohol, benzyl benzoate, dimethyl isosorbide (DMI), dimethyl sulfoxide (DMSO), ethyl acetate, ethyl benzoate, ethyl lactate, glycerol formal, methyl ethyl ketone, methyl isobutyl ketone, N-ethyl-2-pyrrolidone, N-methyl-2-pyrrolidinone (NMP), pyrrolidone-2, tetraglycol, triacetin, tributyrin, tripropionin (tripro) and mixtures thereof. In one embodiment the solvents are DMSO, tripo, NMP and mixtures thereof. These solvents can be maintained in the biodegradable drug delivery composition as part of the formulation or can be evaporated off after fabrication.

The organic solvent in this method for targeting can be present in an amount of 40% to 74% (w %/w %) of the total composition. In another aspect the organic solvent used in the preparation of the biodegradable drug delivery composition is present in an amount of 50% to 60% (w %/w %) of the total composition. In yet another aspect the solvent used in the preparation of the biodegradable drug delivery composition is present in an amount of 60% to 70% (w %/w %) of the total composition or 26% to 90% (w %/w %) of the total composition or 40% to 79% (w %/0/w %/0) of the total composition Some mPEG-OH are contaminated with a small amount of OH-PEG-OH. By following the methods of the present invention and using the contaminated mPEG-OH the final product would be mPEG-PLA contaminated with a small amount of PLA-PEG-PLA, which is encompassed by the present invention.

A method for treating a synovial tissue condition said method comprising administering to a mammal or animal in need of such treatment at least one biodegradable drug delivery composition, as described herein.

The synovial tissue conditions can include any types of arthritis including osteoarthritis, rheumatoid arthritis, gout and rheumatic diseases including ankylosing sondylitis, fibromyalagia, infectious arthritis, juvenile idiopathic arthritis, lupus erythematosus, polymyalgia rheumatica, psoriatic arthritis, reactive arthritis and sclerodoma.

This method for treating is applicable across all synovial joints such as knees, ankles, elbows, humerus, ulna, pivot joints, ball and socket joints, hinge joints, shoulders, scapulas, leg joints, fibula, saddle joints, wrist joints, finger joints and tibia.

The method can be applied to post-surgical applications such as total knee replacements (TKR) or total hip replacements (THR) or non-surgical applications such as intra-articular injection for inflammatory diseases and treatment of infections with antibiotics, which are described herein.

In another aspect, the at least one pharmaceutically active principle can be applied to post-surgical applications which can be, for example, total or partial knee replacements, total or partial hip replacements, total or partial ankle replacements, arthroscopic or open joint surgeries, microfracture, autologous chondrocyte implantation, mosaicplasty, debridement and lavage, ligament repair, tendon repair, rotator cuff repair, meniscus surgery, synovectomy or non-surgical applications by intra-articular injections for inflammatory disease or joint pain.

Another aspect of the present invention is the use of a biodegradable drug composition, as described herein, for targeting at least one pharmaceutically active principle to synovial tissue in a mammal or an animal is yet another aspect of the present invention.

In this use or method of treatment, the polyester can be polylactic acid (PLA), polycaprolactone (PCL), polyglycolic acid (PGA), poly(lactic-co-glycolic acid (PLGA) or polyhydroxyalkanoate (PHA). In one embodiment the polyester that is used is poly(lactic) acid.

The ratio of the biodegradable triblock copolymer of (a) and the biodegradable CA diblock copolymer of (b) is 1:3 to 1:9 in said biodegradable drug composition. In one embodiment the ratio of the biodegradable triblock copolymer of and the biodegradable CA diblock copolymer is selected from the group of 3:2 to 1:19 in this use or method.

In this use or method the length of the polyester chain is defined by its polyester to ethylene oxide molar ratio, which is between 0.5 to 3.5 or 0.5 to 2.5 or 0.5 to 22.3 for the triblock and 3 to 5 or 2 to 6 or 0.8 to 13 for the diblock.

The mass of the end-capped polyethylene glycol can range from 100 Da to 2 kDa or 164 Da to 2 kDa. It can range in the 100 to 300 Da range or in the 1 kDa to 2 kDa range in this use or method.

In this use or method the size of the polyethylene glycol chain ranges from 200 Da to 12 kDa in the biodegradable drug delivery composition or it can range from 400 Da to 12 kDa or 194 Da to 12 kDa.

A number of embodiments and/or aspects of the invention have been described. Nevertheless it will be understood that various modifications may be made without departing from the spirit and scope of the invention.

EXAMPLES

Example 1—Polymer Synthesis

Copolymers were synthesized according to the method described in U.S. Pat. No. 6,350,812, incorporated herein by reference, with minor modifications. Typically the necessary amount of PEG (in the triblock copolymer) or methoxy-PEG (in the diblock copolymer) was heated at 80° C. and dried under vacuum for 30 minutes in a reactor vessel. DL-lactide (corresponding to the targeted LA/ED molar ratio) and zinc lactate (1/1000 of amount of lactide) were added. The reaction mixture was first dehydrated by two short vacuum/ $N_2$ cycles. The reaction was heated at 140° C. under constant nitrogen flow (0.2 bar). After the reaction stopped, the copolymer was discharged from the vessel and left to stand at room temperature until solidification. The product obtained was characterized by $^1$H NMR for its lactate content. The triblock polymers described herein were labelled PxRy where x represents the size of the PEG chain in kDa and y is the LA/ED molar ratio. The diblock mPEG-PLA polymers described herein where labelled dPxRy where x represents the size of the PEG chain in kDa and y is the LA/ED molar ratio.

Example 2—Formulation Preparation Specific for Celecoxib

The formulations described herein were based on organic solution of polymers containing as the drug, celecoxib. Typically, 0.4 grams of polymers, corresponding to a mix of a diblock copolymer and a triblock copolymer in defined mass ratio, were dissolved in 0.57 grams of a biocompatible solvent at room temperature overnight under constant magnetic stirring. The solvent was either a single solvent or a combination of solvents. The next day, 20 mg of celecoxib was added to the polymer solution and stirred until complete dissolution. When the drug was not soluble in the solvent, a suspension of the drug in a polymer solution was obtained. Alternatively, the drug was dissolved or suspended in the biocompatible solvent and the polymer(s) added subsequently. The formulations were loaded in a syringe before use.

Example 3—Formulation Preparation Specific for Other Non-Steroidal Anti-Inflammatory Drugs (NSAIDs)

Following Examples 1 and 2 various formulations are prepared for the following pharmaceutically active principles: etofenamate, celecoxib, apricoxib, rofecoxib, nabumetone, benorilate, etoricoxib, ampiroxicam, aminophemazone, valdecoxib, acetominophen, bufexamac, nimesulide, parecoxib, mefenamic acid, dexibuprofen, ibuprofen, flurbiprofen and ropivicaine.

Example 4—The Formulations that were Prepared for Injection

Following Examples 1 and 2 various formulations were prepared, which are set forth in Table 1 below:

TABLE 1

| Active Principle | % celecoxib | Triblock type | % triblock | Diblock type | % diblock | % Solvent |
|---|---|---|---|---|---|---|
| F14 | 15 | P2R2 | 8 | dP2R2.4 | 32 | 45 DMSO |
| 1 month alternative of F14 No. 1 | 15 | P2R2 | 8 | dP2R2.9 | 32 | 45 DMSO |
| 1 month alternative of F14 No. 2 | 15 | P2R2 | 8 | dP2R3.5 | 32 | 45 DMSO |
| 3 months of F14 | 15 | P2R3.5 | 8 | dP2R3.5 | 32 | 45 DMSO |
| F15 | 10 | P1R3.5 | 10 | dP1R4 | 40 | 40 NMP |
| F16 | 10 | P1R3.5 | 10 | dP1R4 | 40 | 40 DMSO |

Example 5—Injection into Intra-articular Space of a Knee in Sheep

Three sheep per time point were injected with the formulations from F14 in the intra-articular space. Samples of plasma, synovial fluid and synovial tissue were taken at days 0, 1, 7, 14, 28 and 42 from each sheep. The amount of celecoxib (CXB) is measured by LC-MS and determined in each of the targeted locations. The results are shown in the Tables below.

Tables 2, 3 and 4 show the CXB concentrations measured in plasma, synovial fluid and synovial tissue in a first study. CXB was detectable in plasma on Day 1 of the study only. Much higher levels were detected in the synovial fluid on Day 1 and 7 in all animals, but this level was transient and decreased for 14 days until it became undetectable by day 28. Synovial tissue CXB levels were extremely high during the first 7 days, after which there was a slow decrease in CXB tissue levels over 42 days, which however remained present for 90 days.

Celecoxib Concentration in Plasma

TABLE 2

| | CXB concentration (ng/mL) in Plasma | | |
|---|---|---|---|
| Day | Sheep 1 | Sheep 2 | Sheep 3 |
| 0 | BQL | BQL | BQL |
| 1 | 3.94[a] | 12.5 | 9.79 |
| 7 | BQL | BQL | BQL |
| 14 | BQL | BQL | BQL |
| 28 | BQL | BQL | BQL |
| 42 | BQL | BQL | BQL |

BQL—Below the Quantifiable Limit <5.00 ng/mL
[a]Below the Quantifiable Limit, reported as an estimate only Celecoxib Concentration in Synovial Fluid

TABLE 3

CXB concentration (ng/ml) in Synovial Fluid

| Day | Sheep 1 | Sheep 2 | Sheep 3 |
|---|---|---|---|
| 0 | BQL | BQL | BQL |
| 1 | 19,400 | 112,000 | 169,000 |
| 7 | 983 | 138 | 1,100 |
| 14 | BQL | 837 | 4,080 |
| 28 | BQL | BQL | BQL |
| 42 | BQL | BQL | BQL |

BQL—Below the Quantifiable Limit <10.00 ng/mL

Celecoxib Concentration in Synovial Tissue

TABLE 4

CXB concentration (ng/mL) in Synovial Tissue

| Day | Sheep 1 | Sheep 2 | Sheep 3 |
|---|---|---|---|
| 0 | BQL | BQL | BQL |
| 1 | 95,200 | 339,000 | 2,650,000 |
| 7 | 975,000 | 2,600 | 4,370 |
| 14 | 69.5 | 990 | 4,460 |
| 28 | 56.4 | 12,200 | 25.3 |
| 42 | 99.6 | 48.6 | 7.23 |
| 90 | 4.01 [a] | 2.64 [a] | 4.39 [a] |

BQL—Below the Quantifiable Limit <10.00 ng/mL

In a second PK study 3 sheep were used and have the time-points set forth in the tables below. Tables 4, 5 and 6 show the CXB concentrations measured in plasma, synovial fluid and synovial tissue, respectively. CXB was only reliably detectable in plasma on Day 1 of the study. Much higher levels were detected in the synovial fluid on Day 1, but levels decreased substantially over 14 days. Synovial tissue CXB levels were extremely high during the entire 14 days of the study. CXB was detected in the contralateral control knees synovial tissues. Refer to section 14.2.7.5 for raw data.

Celecoxib Concentration in Plasma

TABLE 5

CXB concentration (ng/mL) in Plasma

| Day | Sheep 1 | Sheep 2 | Sheep 3 |
|---|---|---|---|
| 0 | BQL | BQL | BQL |
| 1 | 28.2 | 21.5 | 15.2 |
| 7 | 1.76[a] | 1.38[a] | 2.50[a] |
| 14 | 1.14[a] | 1.27[a] | 0.566[a] |

BQL—Below the Quantifiable Limit <5.00 ng/mL
[a]Below the Quantifiable Limit, hence concentration reported as an estimate only Celecoxib Concentration in Synovial Fluid

TABLE 6

CXB concentration (ng/mL) in Synovial Fluid

| Day | Limb | Sheep 1 | Sheep 2 | Sheep 3 |
|---|---|---|---|---|
| 0 |  | BQL | BQL | BQL |
| 1 | F14 | 191,000 | 145,000 | 220,000 |
|  | Control | 23.0 | — | 47.1 |
| 7 | F14 | 2,250 | 6,870 | 84,700 |
|  | Control | BQL | BQL | BQL |

TABLE 6-continued

CXB concentration (ng/mL) in Synovial Fluid

| Day | Limb | Sheep 1 | Sheep 2 | Sheep 3 |
|---|---|---|---|---|
| 14 | F14 | 132 | 907 | 589 |
|  | Control | BQL | BQL | BQL |

BQL—Below the Quantifiable Limit <10.00 ng/mL

Celecoxib Concentration in Synovial Tissue

TABLE 7

CXB concentration (ng/mL) in Synovial Tissue

| Day | Limb | Sheep 1 | Sheep 2 | Sheep 3 |
|---|---|---|---|---|
| 1 | F14 | 1,010,000 | 3,720,000 | 1,290,000 |
|  | Control | 259 | 1,720 | 361 |
| 7 | F14 | 865,000 | 1,930,000 | 3,190,000 |
|  | Control | 98.3 | 132 | 109 |
| 14 | F14 | 3,700,000 | 1,580,000 | 260,000 |
|  | Control | 662 | — | 102 |

Figure 3:
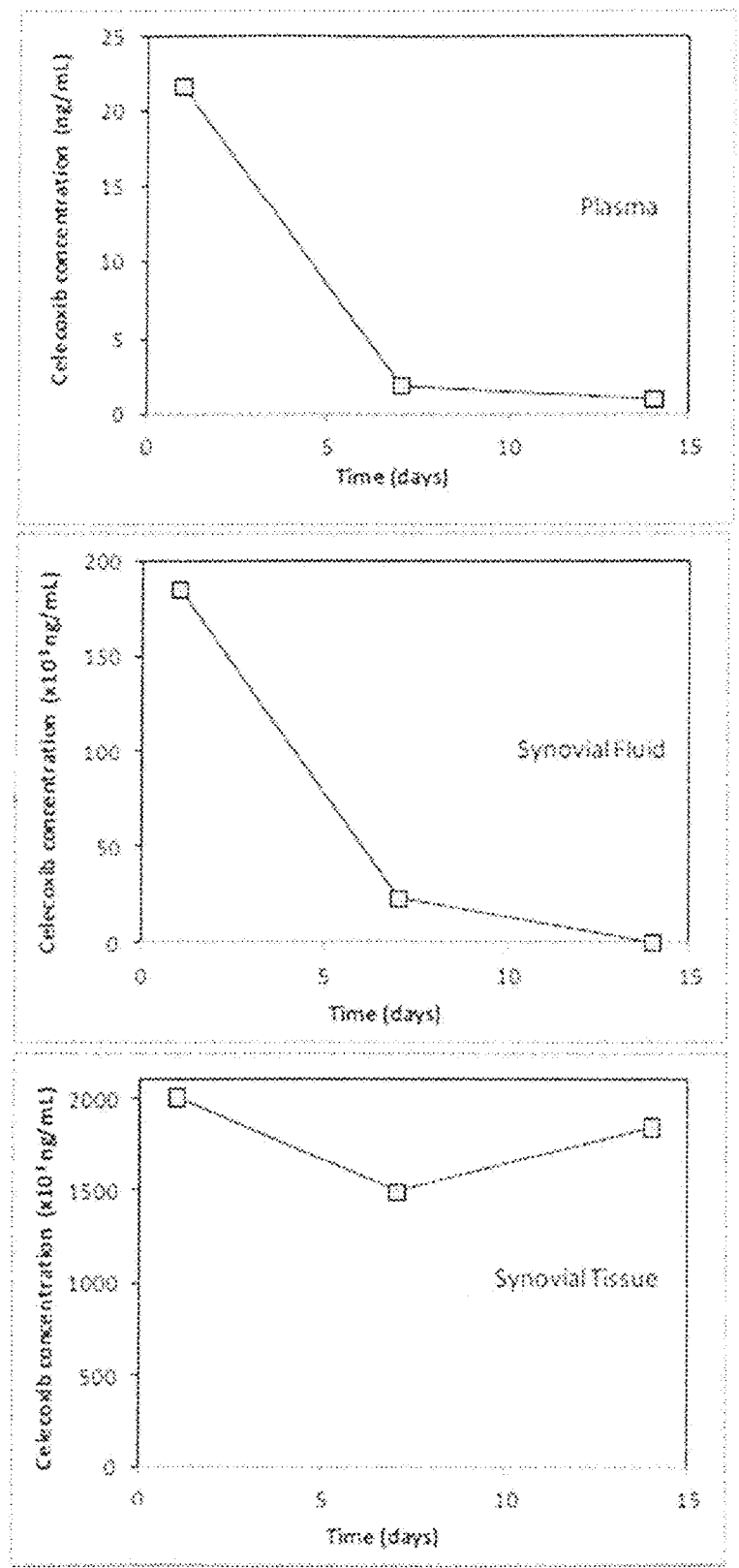
FIG. 3 are graphs showing the pharmacokinetics over time of celecoxib in sheep plasma, synovial fluid and synovial tissues. Synovial tissue maintained extremely high levels of celecoxib over the 14 day study period.
Figure 4:
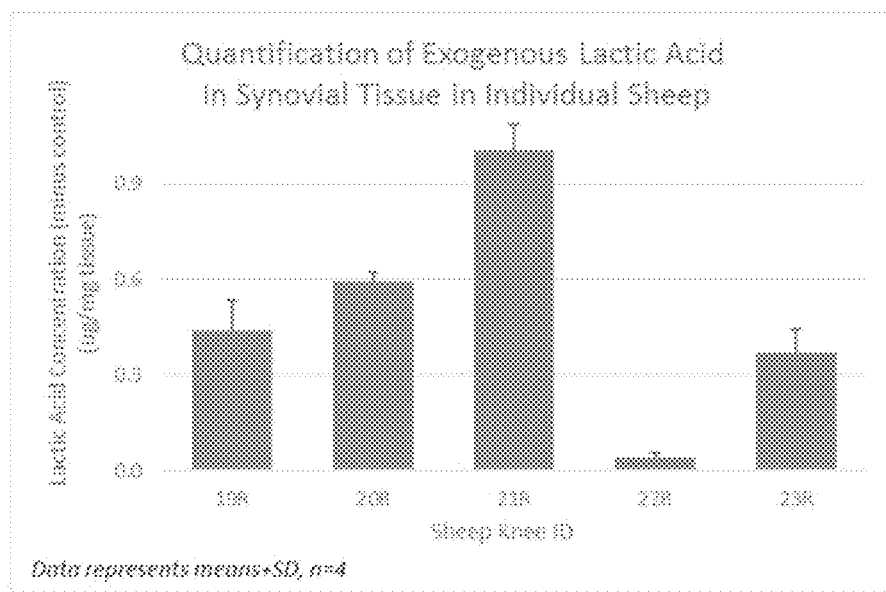
FIG. 4 is a graph showing the quantification of lactic acid in synovial tissue in individual sheep.

The results are shown for the F14 formulation in FIGS. 1 and 3 demonstrating quantitative pharmacokinetic profiles.

A comparison of the formulation F14 with F15 and F16 shows that F14 has superior targeting results to the synovial tissue and synovial fluid, while F15 and F16 did not have such targeting.

Figure 2:
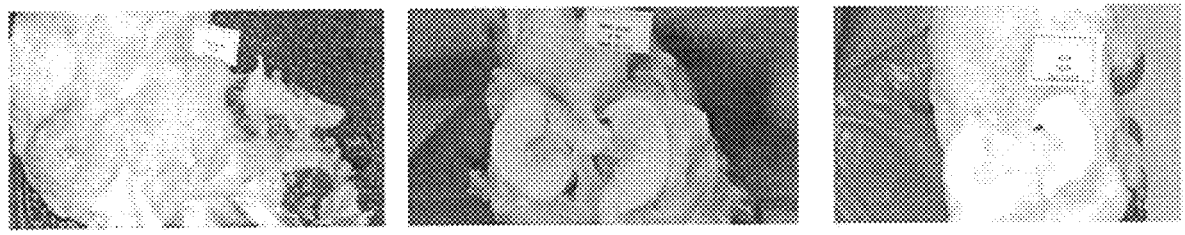
FIG. 2 are macroscopic pictures of F14 in sheep describing the distribution of F14 in sheep knees.

The macroscopic distribution in sheep was undertaken in sheep from day 1 to day 40. The distribution of the celecoxib was clearly demonstrated as illustrated in FIG. 2.

The F14 3 month formulation delivered the celecoxib formulation over this entire time period.

Example 6—Injection into Intra-articular Space of a Knee of A Patient

A plain radiography of patient X's knee is undertaken to evaluate the path of least obstruction and maximal access to the synovial cavity. This access can be superolateral, supermedial or anteromedial/anterolateral. The knee injection site is selected based on the bony anatomy of the patient X's knee joint. In the case of patient X, a superolateral knee injection site is chosen.

Patient X lies supine with the knee fully extended with a thin pad support to facilitate relaxation. The injection site is marked with a pen to leave an impression on the skin and the skin is cleaned with alcohol swabs.

A clinician's thumb is used to gently stabilize the patella while a 25 G 1.5" needle containing the degradable drug delivery composition with celecobix is inserted underneath the supralateral surface of the patella aimed toward the center of the patella and then directed slightly posteriorly and inferomedially into the knee joint. The content of the needle is then injected and the needle is withdrawn from the knee.

Example 7—Quantification of Lactic Acid in Synovial Tissue

Background

This study was conducted to quantify the level of lactic acid in the synovial tissue.

Materials

The synovial tissues from the knee joints of five sheep were used. The left knee joint was untreated, while the right knee joint was treated by injection of 0.6 ml of F14 formulation. This formulation comprised 15% celecoxib as the API, 8% P2R2.2 as the triblock, 32% dP2R2.4 as the diblock and 45% DMSO.

After 7 days in vivo the tissues were retrieved from the sheep and stored in cryovials in a −80° C. freezer until further analysis.

The synovial tissue sample was first weighed and the tissue was transferred into a 50 ml falcon tube. 2 ml of 5M NaOH was added and the falcon tube was left overnight for digestion at 40° C.

The sample was then manually crushed with a spatula and 2 ml of 5N HCl was added and the sample was vortexed to homogenize the solution. The falcon tubes were centrifuged at 4,000 rpm for 10 minutes to obtain a clear supernatant to be used in the assay.

For lactic acid quantification, L- and D-lactic acid enzymatic kits from Megazyme™ were used and the instructions from this kit were followed. Briefly, in a 96-well plate, 20 to 100 μL of supernatant, 50 μL of buffer, 10 μL of NAD+ (nicotinamide-adenine dinucleotide) and 2 μL of GPT (glutamate-pyruvate transaminase) enzyme was added. The plate was then mixed and let standing for three minutes before adding 2 μL of either L- or D-LDH (lactate dehydrogenase) enzyme. The plate was then mixed again and the absorbance at 340 nm was read on a Biotek® microplate reader.

Statistical analysis was conducted using Statistica software (v10, StetSoft).

Results:

The lactic acid concentration for each dilution was compared to other dilutions to determine the poolability of the data. No statistical significance was found across all dilution factors (all p-values >0.7) supporting the pooling of all lactic acid values found for each animal.

The average lactic acid concentration for F14-treated knees compared to saline treated knees was highly statistically significant (p=0.015) (Table 7).

TABLE 8

Lactic acid measured in synovial tissue of sheep* at 7 days post-treatment

|  | F14-treated | Saline-treated | p-value^ |
|---|---|---|---|
| Lactic Acid concentration (ug/mg tissue) | 0.574 ± 0.35 | 0.088 ± 0.05 | 0.015 |

*CORG Study #7300
+Data represents means ± SD, n = 4
^Comparison made using Student's t-test To illustrate the levels of lactic acid in the synovial tissue, FIG. 1 demonstrates solely exogenous lactic acid found in each sheep after subtraction of lactic acid measured in saline-treated controls.

CONCLUSIONS

The statistically significant exogenous lactic acid measured in the synovial tissue using this enzymatic method strongly suggests that the polymer formulation injected into the sheep knees was morselized and targeted to the synovial tissue where it continued to reside at 7 days post-injection.

Example 8—Formulations of Different Compositions

Different compositions were then formulated as set forth in Table 9 below:

TABLE 9

Formulation composition summary

| Formulation | Composition | API | API % | Triblock | Triblock % | Diblock | Diblock % | Solvent | Solvent % |
|---|---|---|---|---|---|---|---|---|---|
| F390 | P2R4/Dp2R4 | Celecoxib | 15% | P2R4 | 8% | Dp2R4 | 32% | DMSO | 45% |
| F391 | P1R4/Dp1R4 | Celecoxib | 15% | P1R4 | 8% | Dp1R4 | 32% | DMSO | 45% |
| F392 | P2R2/Dp1R4 | Celecoxib | 15% | P2R2 | 8% | Dp1R4 | 32% | DMSO | 45% |
| F394 | P1R6/Dp1R4 | Celecoxib | 15% | P1R6 | 8% | Dp1R4 | 32% | DMSO | 45% |
| F396 | P1R4/Dp2R2.4 | Celecoxib | 15% | P1R4 | 8% | Dp2R2.4 | 32% | DMSO | 45% |
| F14 | P2R2/Dp2R2.4 | Celecoxib | 15% | P2R2 | 8% | Dp2R2.4 | 32% | DMSO | 45% |
| F395 | P2R2/Dp2R2.4 | Diclofenac acid | 10% | P2R2 | 8% | Dp2R2.4 | 32% | DMSO | 50% |
| F393 | P2R2/Dp2R2.4 | Bupivacaine base | 5% | P2R2 | 8% | Dp2R2.4 | 32% | DMSO | 55% |

Example 9—Confirmation of Morselization With Different Biodegradable Drug Delivery Compositions To confirm that the different compositions are morselized and targeted to the synovial tissue, 8 different formulations with varying characteristics and APIs were prepared similarly as in Examples 1 and 2 above. Details of composition, triblocks and diblocks used in the formulations are presented in Table 9 above and Tables 10 and 11 below. The mass of the triblock polyethylene glycol and the diblock end-capped polyethylene glycol ranged from 1 to 2 kDa. The lactic acid to ethylene oxide molar ratio ranged from 2 to 6 for the triblock polymers, 2.4 to 4 for the diblock polymers. For both triblocks and diblocks, this ratio range means that the polyester chain length will range from 90 to 182 in terms of degree of polymerization or 6545 g/mol to 13091 g/mol in terms of molar mass.

After preparation the formulations were filter sterilized. Then, each formulation was injected intra-articularly into the knees of adult sheep, where each sheep received one formulation injected bilaterally.

TABLE 10

Description of the formulations triblocks

| Formulation | Composition | Triblock | PEG size (kDa) | Ratio LA/EO | PLA chain length (in degree of polymerization) | PLA chain length (in molar mass (g/mol)) |
|---|---|---|---|---|---|---|
| F14, F393, F395 | P2R2/dP2R2.4 | P2R2 | 2 | 2 | 90.9 | 6545.5 |
| F390 | P2R4/dP2R4 | P2R4 | 2 | 4 | 182 | 13091 |
| F391 | P1R4/dP1R4 | P1R4 | 1 | 4 | 90.9 | 6545.5 |
| F392 | P2R2/dP1R4 | P2R2 | 2 | 2 | 90.9 | 6545.5 |
| F394 | P1R6/dP1R4 | P1R6 | 1 | 6 | 136.4 | 9818.2 |
| F396 | P1R4/dP2R2.4 | P1R4 | 1 | 4 | 90.9 | 6545.5 |

TABLE 11

Description of the formulations diblocks

| Formulation | Composition | Diblock | mPEG size (kDa) | Ratio LA/EO | PLA chain length (degree of polymerization) | PLA chain length (g/mol) |
|---|---|---|---|---|---|---|
| F14, F393, F395 | P2R2/dP2R2.4 | dP2R2.4 | 2 | 2.4 | 109.1 | 7854.5 |
| F390 | P2R4/dP2R4 | dP2R4 | 2 | 4 | 182 | 13091 |
| F391 | P1R4/dP1R4 | dP1R4 | 1 | 4 | 90.9 | 6545.5 |
| F392 | P2R2/dP1R4 | dP1R4 | 1 | 4 | 90.9 | 6545.5 |
| F394 | P1R6/dP1R4 | dP1R4 | 1 | 4 | 90.9 | 6545.5 |
| F396 | P1R4/dP2R2.4 | dP2R2.4 | 2 | 2.4 | 109.1 | 7854.5 |

To confirm morselization and synovial tissue targeting of other formulations, the formulations were prepared as in Examples 1 and 2 using the formulations set forth in Table 9. After preparation the formulations were all filter sterilized. 6 sheep total were used and bilateral injections were performed in 12 knees. The sheep treatment groups are set forth in Table 12 below:

TABLE 12

Sheep treatment groups

| Group | n | Bilateral IA injection | Sacrifice |
|---|---|---|---|
| 1 | 1 | F390-Celecoxib 15% | 7 days |
| 2 | 1 | F391-Celecoxib 15% | 7 days |
| 3 | 1 | F392-Celecoxib 15% | 7 days |
| 4 | 1 | F393-Bupivicaine 5% | 7 days |
| 5 | 1 | F394-Celecoxib 15% | 7 days |
| 6 | 1 | F350-Diclofenac 10% | 7 days |
| 7 | 1 | F395-Celecoxib 15% | 7 days |
| 8 | 1 | F14 - Celecoxib 15% | 7 days |

After sacrifice at 7 days, the knees were surgically opened and macroscopically observed to determine morselization behaviour of each formulation by qualitatively examining particle size and disposition. Morselization or lack thereof was photodocumented, aided by D&C GREEN #6 dye within the formulation which rendered the composition visibly blue.

CONCLUSIONS

Morselization was observed when the triblock (F392) or the diblock (F396) was composed of 2 kDa PEGs. Formulations with 2 kDa PEGs in both their triblocks and diblocks led to depots showing morselization, regardless of their PLA chain length (F390, F14)).

Different APIs (e.g., Celecoxib, Diclofenac or Bupivacain) were shown to result in similar morselization and distribution throughout the joint. Diclofenac and bupivacaine-based formulations have morselized and distributed faster than Celecoxib-based ones, likely due to the lower formulation viscosity observed with these APIs.

Example 10—Formulation Preparation Specific for Celecoxib

The formulations described herein were based on an organic solution of polymers containing the drug, celecoxib. Typically, 0.4 grams of polymers, corresponding to a mix of a diblock copolymer and a triblock copolymer in defined mass ratio, were dissolved in 0.4 grams of a biocompatible solvent (e.g., DMSO) at room temperature overnight under constant magnetic stirring. The solvent was either a single solvent or a combination of solvents. The next day, 0.02 grams of celecoxib was added to the polymer solution and stirred until complete dissolution. When the drug was not soluble in the solvent, a suspension of the drug in a polymer solution was obtained. Alternatively, the drug was dissolved or suspended in the biocompatible solvent and the polymer(s) added subsequently. The formulations were loaded in a syringe before use.

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the claims, including equivalents thereof.

The invention claimed is:

1. A method for morselizing a biodegradable drug delivery composition comprising at least one pharmaceutically active principle comprising:
   (1) formulating a biodegradable drug composition comprising
   (a) a biodegradable triblock copolymer having the formula:

   $PLA_v\text{-}PEG_w\text{-}PLA_x$ wherein v and x are the number of repeat units ranging from 24 to 682 and w is the number of repeat units ranging from 4 to 273 and v=x or v≠x;
   (b) a biodegradable diblock copolymer having the formula:

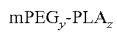
   $mPEG_y\text{-}PLA_z$ wherein y and z are the number of repeat units with y ranging from 3 to 45 and z ranging from 7 to 327, wherein the polyethylene glycol chain in the triblock and/or the diblock copolymer is 2 kDa and
   wherein the ratio of the biodegradable triblock copolymer of (a) and the biodegradable diblock copolymer of (b) is 3:2 to 1:19 in said biodegradable drug composition and
   (c) at least one pharmaceutically active principle;
   (2) administering said formulated biodegradable drug delivery composition in at least one joint of a patient, such that it is contained within the articulating joint capsule.

2. The method for morselizing according to claim 1, wherein said formulation of said biodegradable drug delivery composition is taken up by syringe for administration and injected into said joint or manually formed into a solid bolus by exposing the formulation to aqueous liquid and manual placement into the joint.

3. The method for morselizing according to claim 1, wherein said formulation of said biodegradable drug delivery composition is subjected to a mechanical challenge.

4. The method for morselizing according to claim 3, wherein said mechanical challenge is obtained by internal structures of the joints, articulation, weight bearing and/or by synovial tissue pressure.

5. The method for morselizing according to claim 1, wherein the formulation of said biodegradable drug delivery composition is broken into pieces.

6. The method for morselizing according to claim 1, wherein said at least one pharmaceutically active principle is present in said formulation in an amount of 1% to 85% w%/w%.

7. The method for morselizing according to claim 1, wherein the polylactic repeat unit to ethylene oxide molar ratio is 1.6 to 7.2 in the triblock and 1.9 to 4.8 in the diblock.

8. The method for morselizing according to claim 1, wherein the degree of polymerization in the triblock equal to v+w+x is 72 to 324 and the degree of polymerization in the diblock equal to y+z is 85.5 to 216.

9. The method for morselizing according to claim 1, wherein the triblock is present in an amount of 6% to 24% (wt %/wt %) and the diblock is present in an amount of 12% to 40% (wt %/wt %).

10. The method for morselizing according to claim 1, wherein the step of formulating said biodegradable drug composition further comprises mixing the triblock copolymer with the diblock copolymer in a biocompatible organic solvent to form a triblock copolymer and diblock copolymer mixture.

11. The method for morselizing according to claim 10, wherein the step of formulating the biodegradable drug composition further comprises adding to said triblock copolymer and diblock copolymer mixture the at least one pharmaceutically active principle.

12. The method for morselizing according to claim 10, wherein the solvent is evaporated off in the step of formulating the biodegradable drug composition.

13. The method for morselizing according to claim 11, wherein the step of formulating the biodegradable drug composition further comprises exposing said triblock copolymer and diblock copolymer mixture to an aqueous liquid to form a solid bolus.

14. The method for morselizing according to claim 5, wherein said pieces are broken down to smaller and smaller pieces.

15. The method according to claim 1, wherein said at least one pharmaceutically active principle can be applied to post-surgical applications which are total knee replacements (TKR), total hip replacements (THR), joint surgeries, arthroscopic joint surgeries, open joint surgeries or non-surgical applications such as intra-articular injection for inflammatory diseases, mosaicplasty, microfracture, autologous chondrocyte implantation, osteoarticular transfer system, ligament and tendon repair, meniscus repair or unicompartmental knee replacement.

16. The method according to claim 1, wherein the at least one pharmaceutically active principle can be applied to post-surgical applications which are total or partial knee replacements, total or partial hip replacements, total or partial ankle replacements, arthroscopic or open joint surgeries, microfracture, autologous chondrocyte implantation, mosaicplasty, debridement and lavage, ligament repair, tendon repair, rotator cuff repair, meniscus surgery, synovectomy or non-surgical applications by intra-articular injections for inflammatory disease or joint pain.

17. The method for morselizing according to claim 1, wherein said administration to said patient is 0.1 to 6 ml for the knee, 0.1 to 6 ml for the hip, 0.1 to 4 ml for the ankle, 0.1 to 6 ml for the shoulder and 0.1 to 2 ml for the elbow.

18. The method according to claim 1, wherein said at least one pharmaceutically active principle is a peptide drug, a protein drug, a desensitizing agent, an antigen, a non-steroidal anti-inflammatory agent, an anti-inflammatory drug, an anaesthetic, an anti-oxidant agent, an anti-infective agent, a chemotherapeutic agents, an anti-nociceptive agent, a disease modifying osteoarthritis drug (DMOAD), anabolic agents, anti-catabolic agents, autophagy regulation agents, anti-osteoclast-mediated bone loss agents, nutraceutical agents, analgesic agents, biologics and mixtures thereof.

19. The method according to claim 18, wherein said non-steroidal anti-inflammatory agent is etofenamate, celecoxib, apricoxib, rofecoxib, nabumetone, benorilate, etoricoxib, ampiroxicam, aminophemazone, valdecoxib, acetominophen, bufexamac, nimesulide, parecoxib, mefenamic acid, dexibuprofen, ibuprofen, flurbiprofen, aspirin, dexketoprofen, diclofenac, diflunisal, etodolac, fenoprofen, firocoxib, indomethacin, ketoprofen, ketorolac, lornoxicam, loxoprofen, loxomac, lumiracoxib, meclofenamic acid, meloxicam, naproxen, naprosyn, nimalox, oxaporozin, piroxicam, salsalate, sulindac, tenoxicam, tolfenamic acid, ropivicaine and mixtures thereof.

* * * * *

UNITED STATES PATENT AND TRADEMARK OFFICE
CERTIFICATE OF CORRECTION

PATENT NO. : 11,865,205 B2  
APPLICATION NO. : 17/156781  
DATED : January 9, 2024  
INVENTOR(S) : Georges Gaudriault et al.

Page 1 of 2

It is certified that error appears in the above-identified patent and that said Letters Patent is hereby corrected as shown below:

In the Specification

Column 12; Line 11:  
Change:  
"decoxib, acetominophen, bufexamac, nimesulide, pare-"  
To:  
-- decoxib, acetaminophen, bufexamac, nimesulide, pare- --

Column 19; Line 44:  
Change:  
"acetominophen, bufexamac, nimesulide, parecoxib,"  
To:  
-- acetaminophen, bufexamac, nimesulide, parecoxib, --

Column 24; Lines 3-5:  
Change:  
"zone, valdecoxib, acetominophen, bufexamac, nimesulide, parecoxib, mefenamic acid, dexibuprofen, ibuprofen, flurbiprofen and ropivicaine."  
To:  
-- zone, valdecoxib, acetaminophen, bufexamac, nimesulide, parecoxib, mefenamic acid, dexibuprofen, ibuprofen, flurbiprofen and ropivacaine. --

In the Claims

Column 32; Lines 57-58; Claim 19:  
Change:  
"coxib, ampiroxicam, aminophemazone, valdecoxib, acetominophen, bufexamac, nimesulide, parecoxib, mefenamic"

Signed and Sealed this  
Thirteenth Day of January, 2026

John A. Squires  
*Director of the United States Patent and Trademark Office*

To:
-- coxib, ampiroxicam, aminophemazone, valdecoxib, acetaminophen, bufexamac, nimesulide, parecoxib, mefenamic --

Column 32; Line 65; Claim 19:
Change:
"ropivicaine and mixtures thereof."
To:
-- ropivacaine and mixtures thereof. --